(12) United States Patent
Devierre et al.

(10) Patent No.: US 7,566,300 B2
(45) Date of Patent: Jul. 28, 2009

(54) ENDOSCOPIC SURGICAL ACCESS DEVICES AND METHODS OF ARTICULATING AN EXTERNAL ACCESSORY CHANNEL

(75) Inventors: Jacques Devierre, Genappe (BE); Kenneth C. Kennedy, II, Clemmons, NC (US)

(73) Assignee: Wilson-Cook Medical, Inc., Winston-Salem, NC (US)

( * ) Notice: Subject to any disclaimer, the term of this patent is extended or adjusted under 35 U.S.C. 154(b) by 588 days.

(21) Appl. No.: 11/107,455

(22) Filed: Apr. 15, 2005

(65) Prior Publication Data

US 2005/0234297 A1    Oct. 20, 2005

Related U.S. Application Data

(60) Provisional application No. 60/562,689, filed on Apr. 15, 2004.

(51) Int. Cl.
*A61B 1/00* (2006.01)
(52) U.S. Cl. .................................. 600/104; 600/106
(58) Field of Classification Search ............. 600/104, 600/106, 107, 114, 136, 137, 139, 141, 142, 600/153
See application file for complete search history.

(56) References Cited

U.S. PATENT DOCUMENTS

| | | | |
|---|---|---|---|
| 1,500,798 | A | 7/1924 | Campodonico |
| 3,173,414 | A | 3/1965 | Guillant |
| 5,050,585 | A * | 9/1991 | Takahashi .................. 600/123 |
| 5,230,622 | A | 7/1993 | Brossoit |
| 5,599,304 | A * | 2/1997 | Shaari ..................... 604/94.01 |

(Continued)

FOREIGN PATENT DOCUMENTS

DE    29602860    2/1996

(Continued)

OTHER PUBLICATIONS

Search Report and Written Opinion, dated Mar. 27, 2006, for International Application No. PCT/US2005/012874.

(Continued)

*Primary Examiner*—Linda C Dvorak
*Assistant Examiner*—Alireza Nia
(74) *Attorney, Agent, or Firm*—Brinks Hofer Gilson & Lione

(57) ABSTRACT

Devices and methods for detachably engaging an insertion section of an endoscope and selectively articulating an endoscopic surgical access channel are provided. A device comprises an articulating main body having a stationary first body, an articulatable second body, and coupler having a mounting member and an articulation link member configured to articulatively couple the second body to the first body. The stationary first body has a distal end, a proximal end, and a first longitudinal axis. The articulatable second body has a proximal opening and a distal opening defining an accessory channel member passageway, the distal opening having a second longitudinal axis oriented toward a space exterior to the first body distal end, wherein the second body longitudinal axis is capable of articulating relative to the first body longitudinal axis. The devices and methods, as taught herein, provide control over the position and/or orientation of a diagnostic, monitoring, scope, sewing device, cutting device, suturing device, forceps, grabbing device, instrument, or other tool within the visual field beyond the distal opening of the endoscope.

30 Claims, 18 Drawing Sheets

U.S. PATENT DOCUMENTS

| | | | |
|---|---|---|---|
| 5,749,889 | A | 5/1998 | Bacich et al. |
| 5,797,835 | A * | 8/1998 | Green .................. 600/106 |
| 5,931,848 | A * | 8/1999 | Saadat .................. 606/167 |
| 6,022,313 | A | 2/2000 | Ginn et al. |
| 6,071,233 | A | 6/2000 | Ishikawa et al. |
| 6,179,776 | B1 | 1/2001 | Adams et al. |
| 6,352,503 | B1 | 3/2002 | Matsui et al. |
| 6,878,106 | B1 * | 4/2005 | Herrmann .............. 600/104 |
| 2002/0049367 | A1 | 4/2002 | Irion et al. |
| 2002/0107530 | A1 | 8/2002 | Sauer et al. |
| 2003/0040657 | A1 | 2/2003 | Yamaya et al. |
| 2003/0130564 | A1 | 7/2003 | Martone et al. |
| 2004/0068232 | A1 * | 4/2004 | Hart et al. .......... 604/167.06 |

FOREIGN PATENT DOCUMENTS

| | | |
|---|---|---|
| GB | 2109241 | 6/1983 |

OTHER PUBLICATIONS

Notification of Transmittal of the International Preliminary Report on Patentability, dated Oct. 10, 2006, from the International Preliminary Examining Authority.

The "LSI Product" by LSI Solutions and sold by Wilson-Cook Medical Inc. prior to Apr. 15, 2004 (one-page color photograph).

* cited by examiner

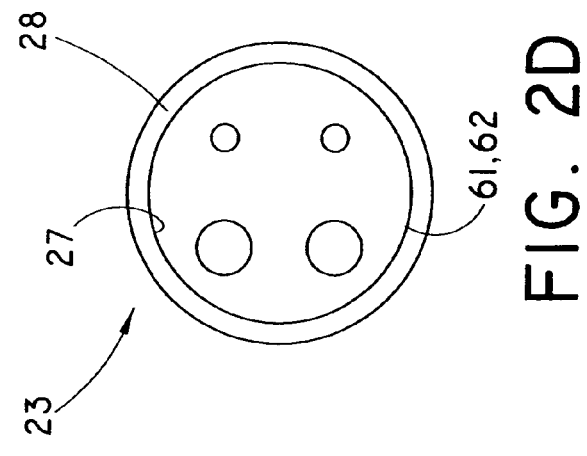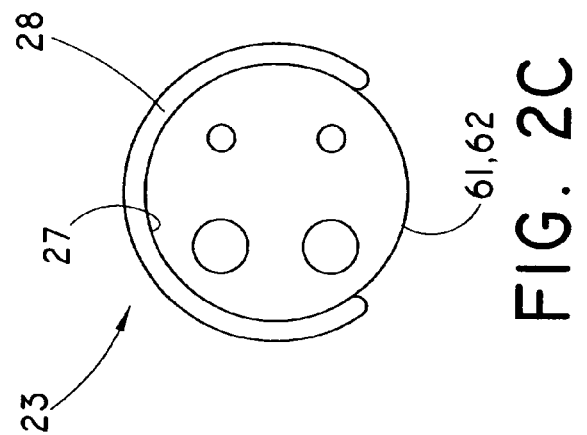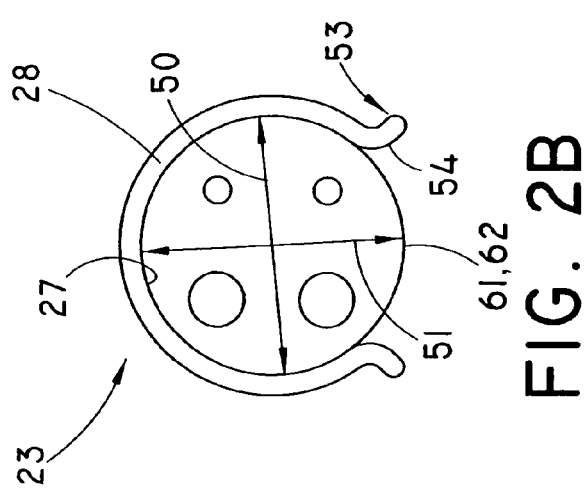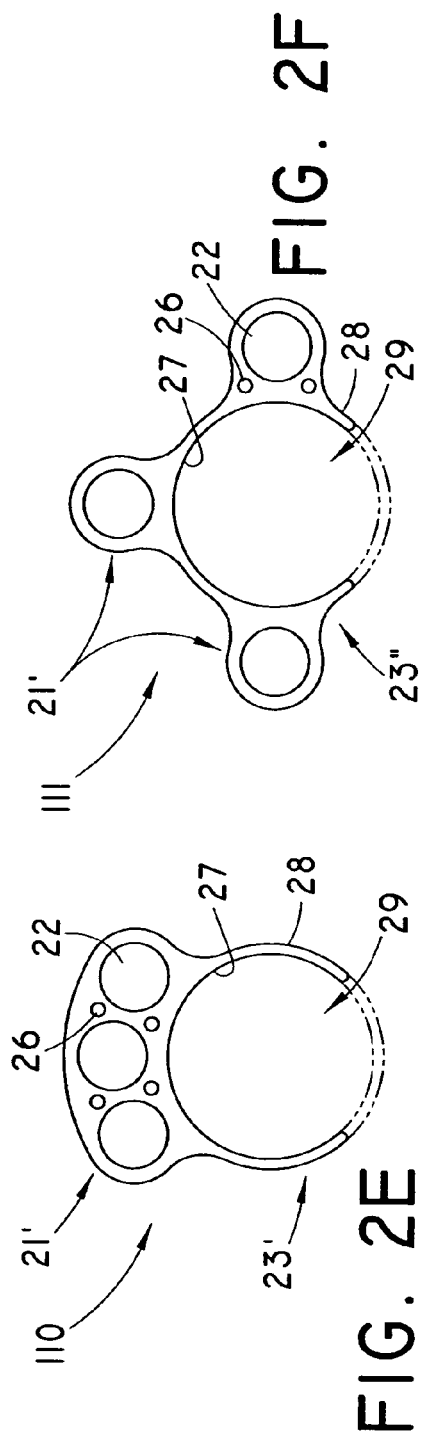

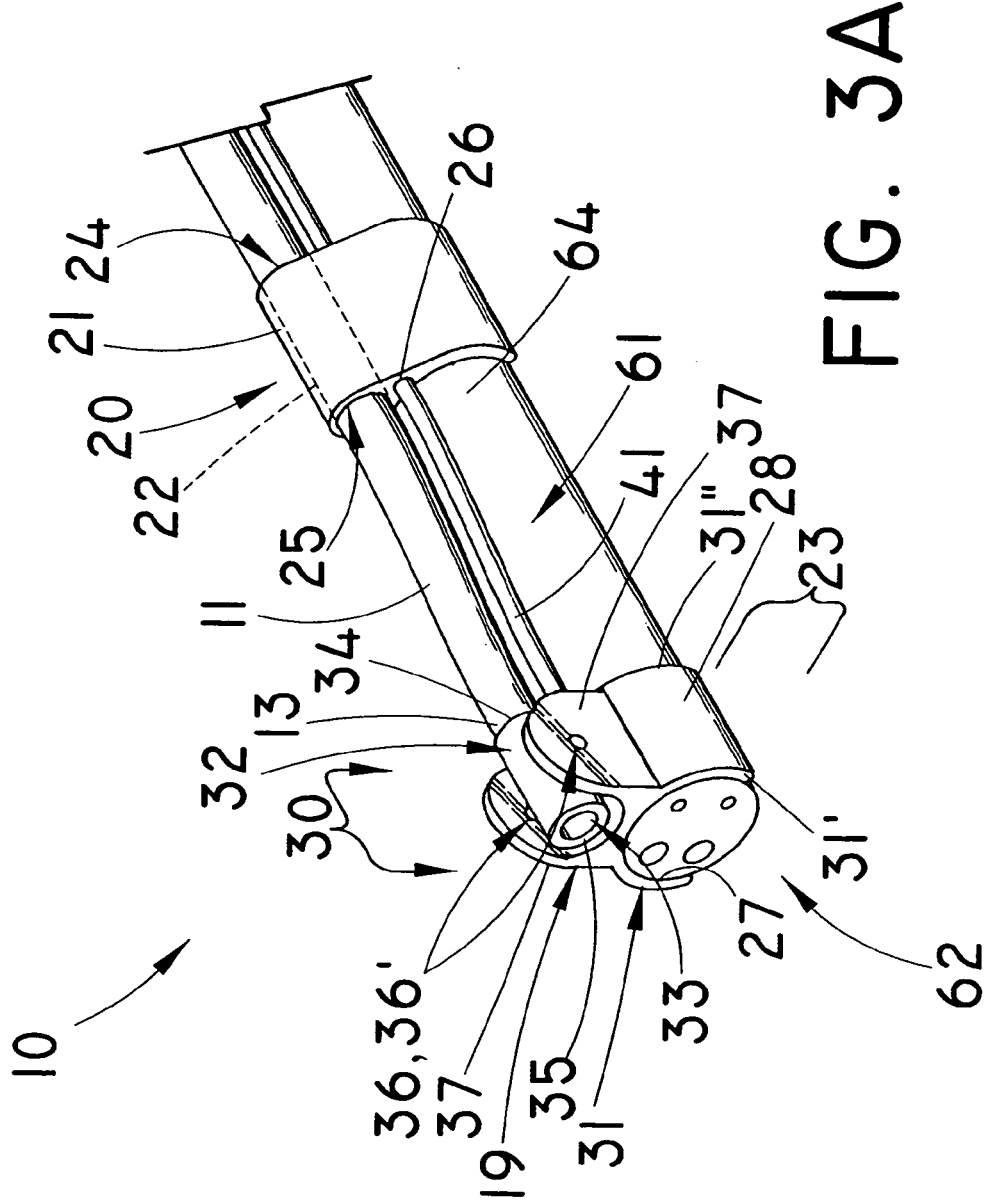

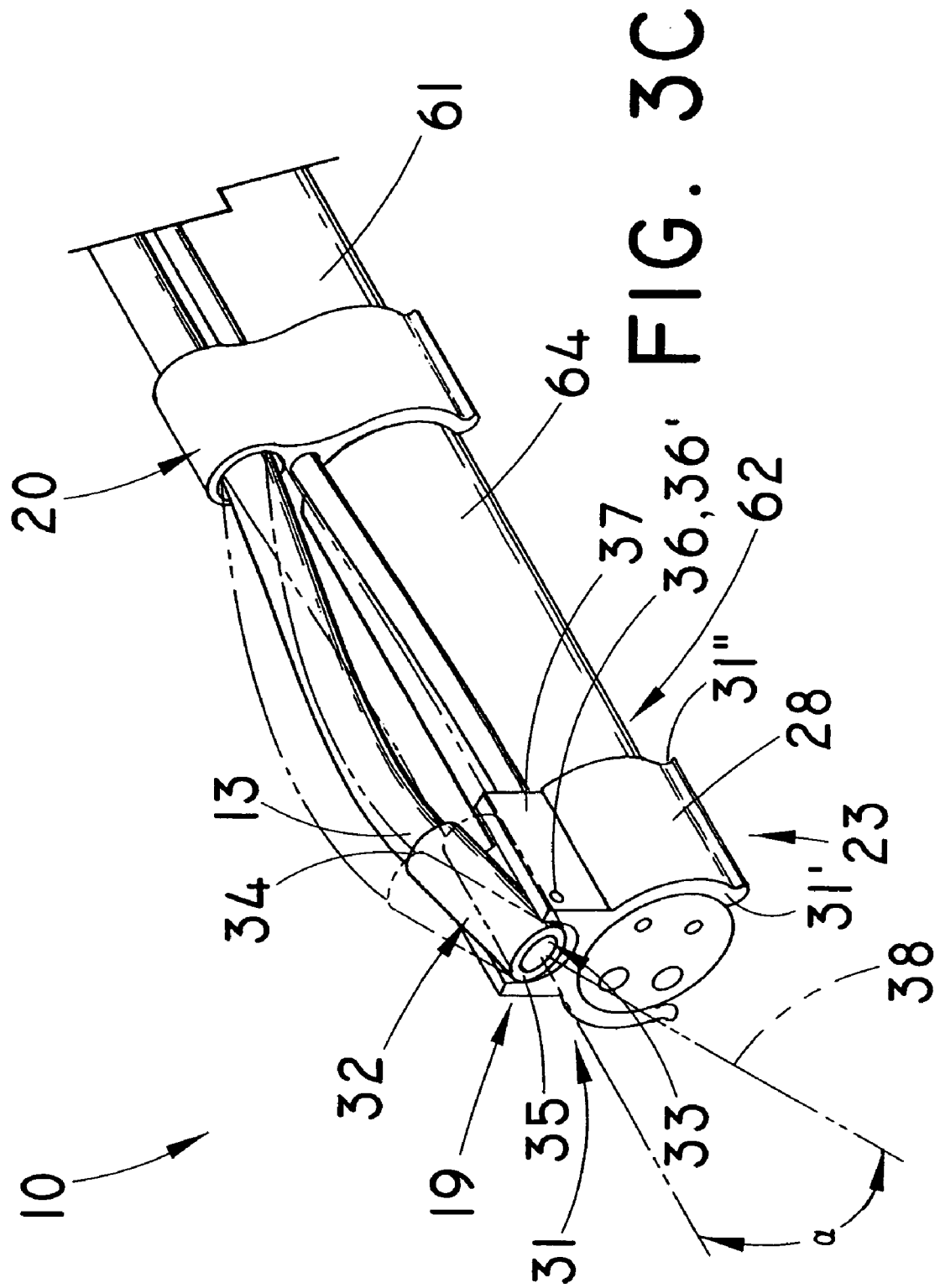

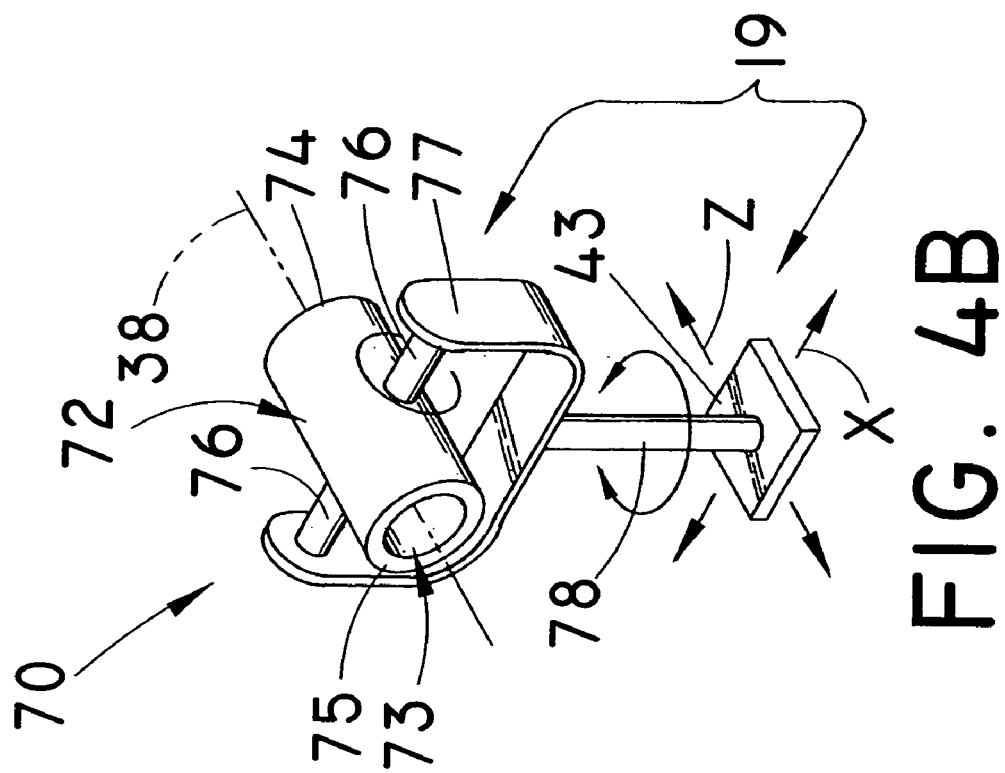
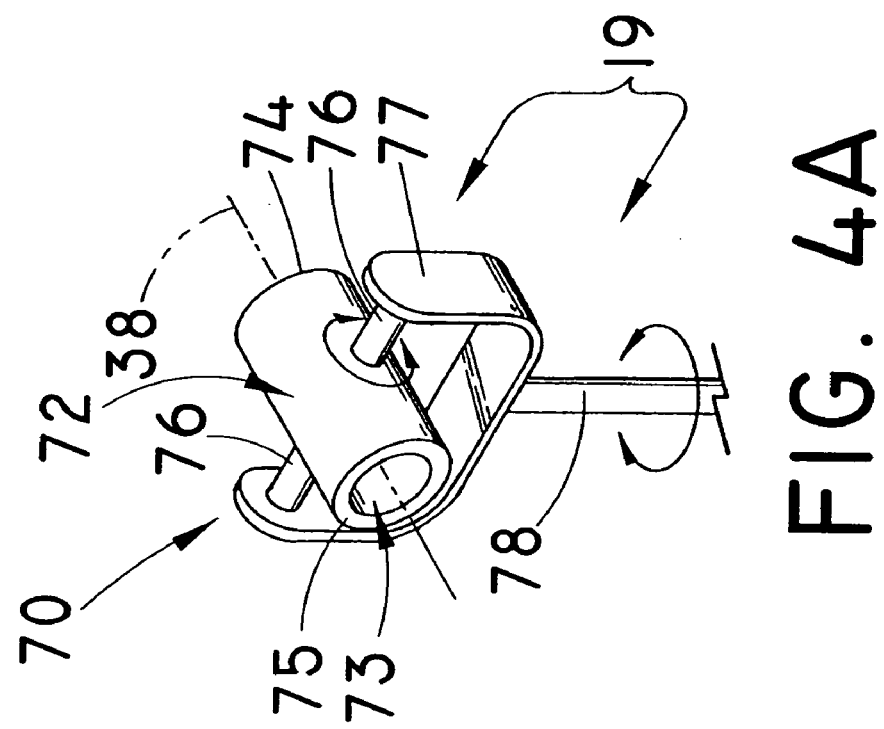

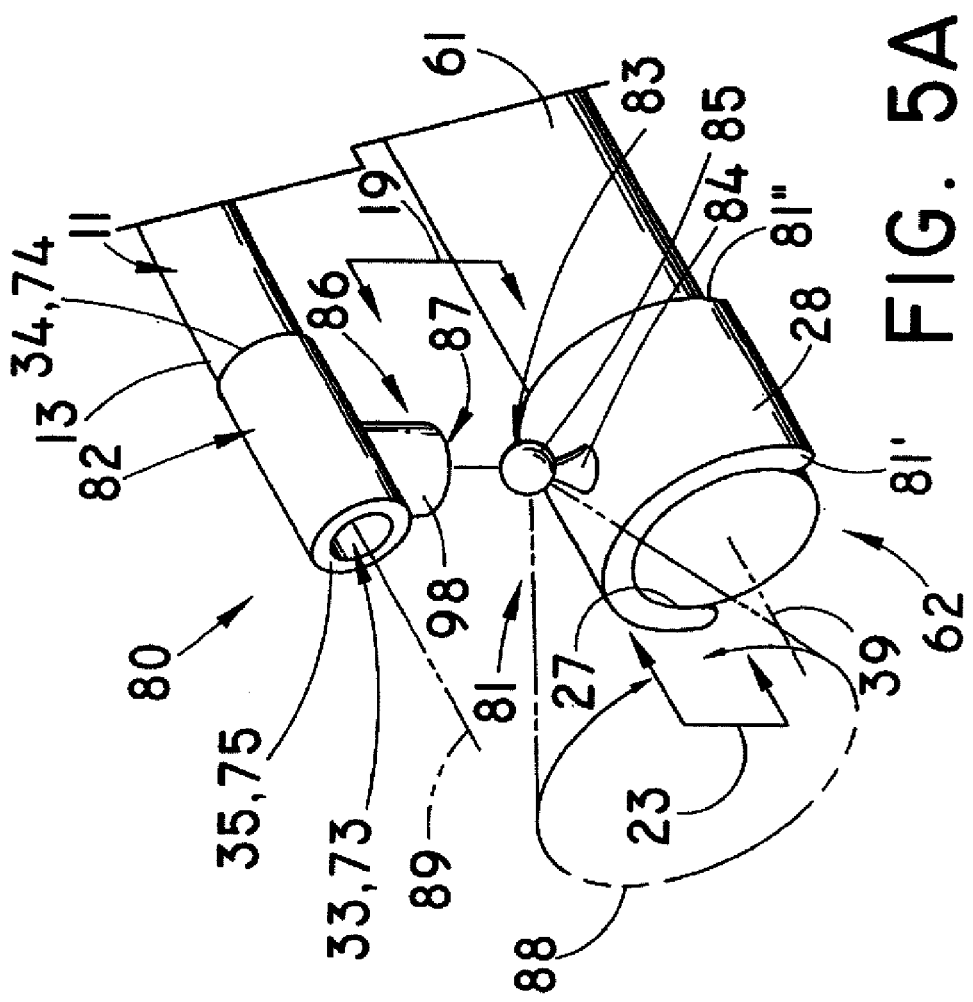

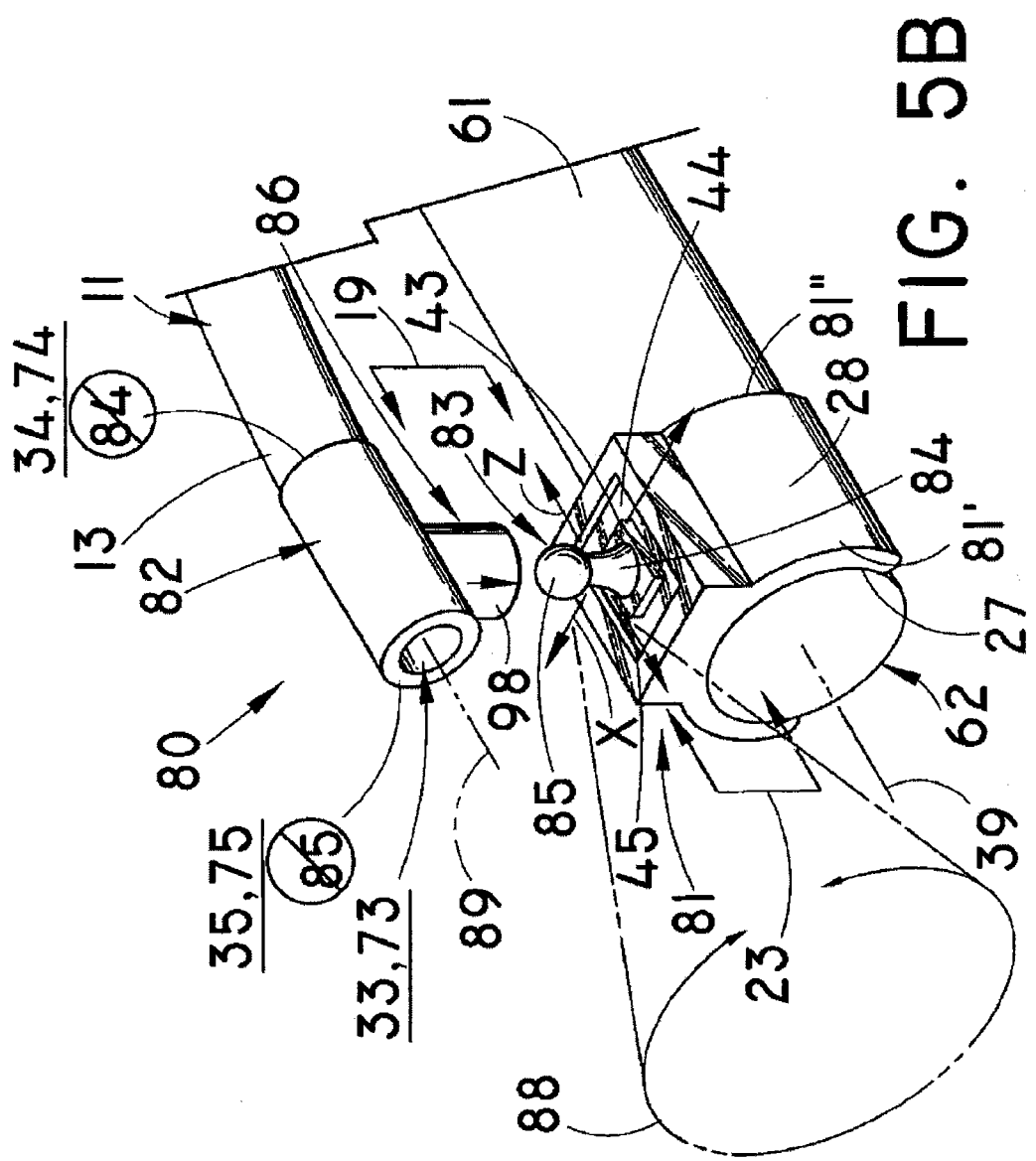

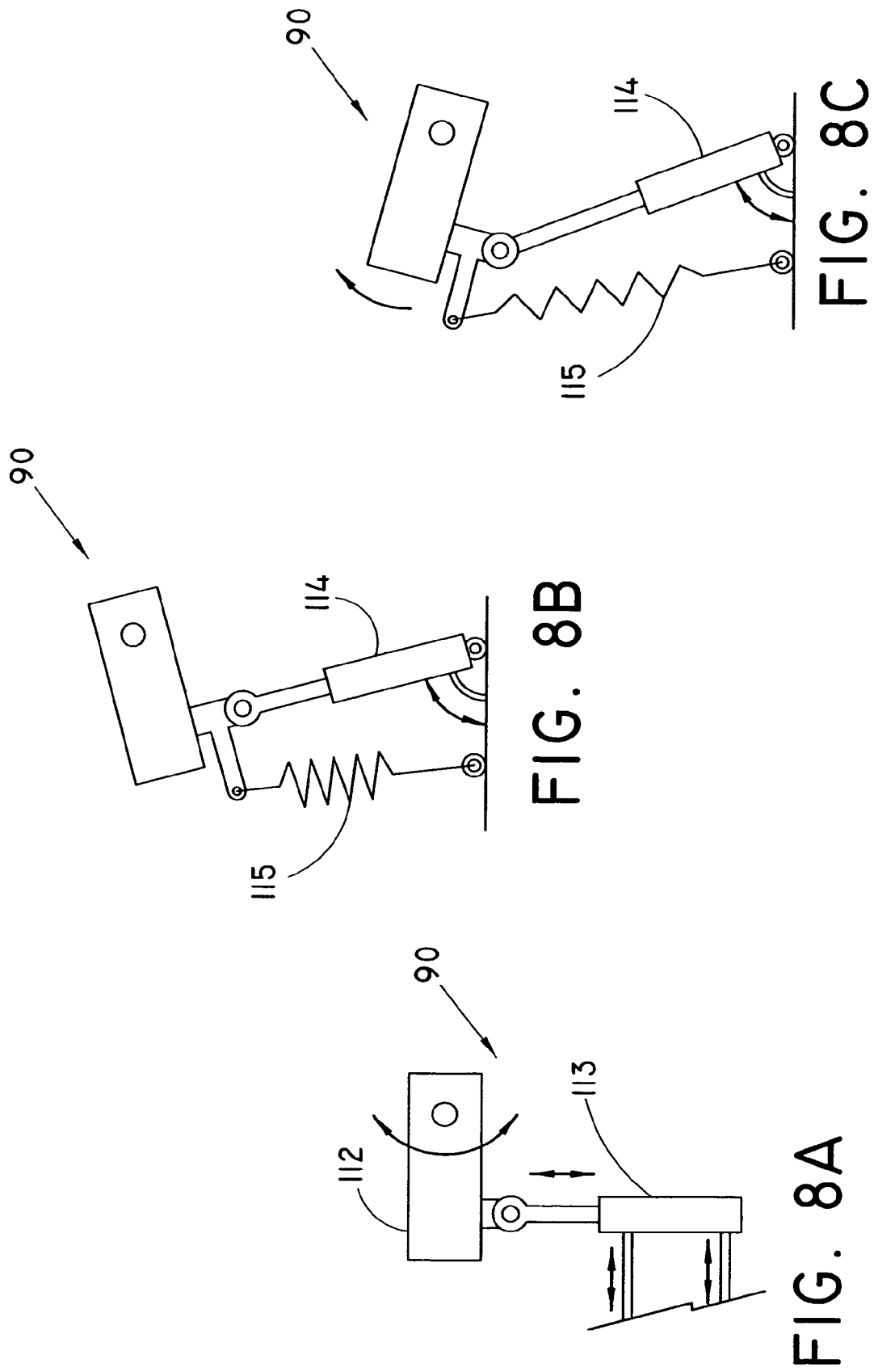

ENDOSCOPIC SURGICAL ACCESS DEVICES AND METHODS OF ARTICULATING AN EXTERNAL ACCESSORY CHANNEL

RELATED APPLICATIONS

The present patent document claims the benefit of the filing date under 35 U.S.C. § 119(e) of provisional U.S. patent application Ser. No. 60/562,689, filed on Apr. 15, 2004, which is hereby incorporated by reference in its entirety.

FIELD OF THE INVENTION

The present invention relates to medical devices generally in the field of endoscopic surgery, and in particular to medical devices by which accessories may be positioned for use with an endoscope.

BACKGROUND

Endoscopic surgery has seen rapid growth over the past decade. By way of background, a conventional endoscope generally is an instrument with a light source and image sensor for visualizing the interior of an internal region of a body. A wide range of applications have been developed for the general field of endoscopes including by way of example the following: arthroscope, angioscope, bronchoscope, choledochoscope, colonoscope, cytoscope, duodenoscope, enteroscope, esophagogastro-duodenoscope (gastroscope), laparoscope, laryngoscope, nasopharyngo-neproscope, sigmoidoscope, thoracoscope, and utererscope (individually and collectively, "endoscope"). In order to form an image of the scene under observation, a light source and image sensor are features that may be provided at or near the distal end portion of an insertion section of the endoscope that is to be inserted into the body, where the term "distal end portion" includes a distal end face—as well as a side of the distal section of—the insert portion of the endoscope. Endoscopes may also incorporate additional functionality for observation or operation within the body, such as a working channel for passing diagnostic, monitoring, treatment, or surgical tools through the endoscope, where the working channel has an opening located at the distal end portion of the insert.

The advantages of minimally invasive surgery performed with the help of an endoscope are well known and understood in the medical field. As a result, there have been a growing number of devices for use with endoscopes for delivering, for example, diagnostic, monitoring, treatment, operating instruments, tools, and accessories (collectively, "tools") into the observation field and working space of the physician's endoscope.

Some of the endoscopic devices on the market are short and stiff while others are long and flexible. In either case, the devices normally utilize tubes from which the tools may extend or exit. These tubes are typically coupled to the endoscope at or near the distal end portion of the endoscope insertion section (the "insert") by an attachment tip that does not articulate.

Rather, the attachment tip as known and presently used in the market of endoscope accessories is merely formed from an integral piece of plastic with a lumen. Thus, the attachment tip is affixed to the endoscope in an immovable manner, e.g., elastic band or with medical grade tape having an adhesive layer or other means such as glue to hold the attachment tip and distal end portion of the endoscope insertion section together.

The lumen of the attachment tip is typically co-axial with, parallel with, or at a fixed angle relative to, the distal end portion of the insert. This is also true in the case of an endoscope that has a working channel at the distal end portion of the insert, whereby the attachment tip lumen is co-axial, parallel, or angularly fixed with respect to the distal opening of the working channel. Regardless of whether the insert has a working channel or not, the attachment tip is constrained to the side of the endoscope insertion section and does not move independently thereof. Thus, for a flexible endoscope, when the distal end portion of the insert is flexed or bent, then the attachment tip will move in accordance with the movement of the distal end portion. Conversely, when the distal end portion of the insert remains stationary, the attachment tip likewise remains stationary. Otherwise stated, there is no independent moveable part in the conventional attachment tip that permits articulation of the attachment tip lumen independent of and relative to the distal end portion of the insert.

Consequently, tools exiting or extending from a distal opening in the attachment tip (or from the accessory tubing) do so in a fixed orientation that is substantially aligned with (or angularly fixed relative to) the distal end portion of the insert. The physician is therefore unable to manipulate the attachment tip into position independent of the insert's distal end portion, and one of the few parameters available for positioning the tool may be the depth to which the tool exits and extends beyond the attachment tip, where the tool may droop or drift into the visual field of the endoscope. An alternative parameter is that the tool may be comprised of a memory material or may be carried in a wire member sheath having a natural deflected state and elastic memory to return the wire member sheath (or the tool) to a deflected state. The tool or wire member sheath is coupled to the side of the distal end portion of the insert and, as the tool or sheath is extended beyond a distal tip of the insert, the tool or wire member returns to its elastic memory (i.e., a bended deflected state that curves or defects away from, or toward, the observation field). However, the elastic tool may be difficult for the physician to control in the observation field and working space, and a curved wire member sheath of this type may extend into and obstruct the observation field and working space of the physician's endoscope and/or the visualization of the tool.

In other cases, it is the insert that may articulate. The insert may include articulation control means for manipulating the position of the distal end portion into an articulating (e.g., bending and flexing) position. For those inserts incorporating a working channel built into the endoscope or incorporated into a sheath that fits to or encapsulates the distal end portion of the insert, it is still nevertheless the insert that articulates. The working channel from which a tool exits or extends moves with the movement of the insert and not independently thereof.

For the foregoing reasons, it is desirable to have an endoscopic surgical access device, as taught herein, that gives the physician control over the position and/or orientation of the tool within the visual field of the distal end portion of the insert.

SUMMARY OF THE INVENTION

An endoscopic surgical access device is provided. In one embodiment, the device has a first body, a second body, and a coupler. The first body has a holding member for detachably engaging an insertion section of an endoscope at or near a distal end of the insertion section. The second body includes a distal end opening and a passageway. The coupler joins the second body to the first body so that the second body may articulate relative to the first body.

In another embodiment, the device according to the invention comprises a base having a holding member with proximal and distal apertures defining a cavity and a first longitudinal axis. The holding member cavity is sized for detachably engaging an insertion section of an endoscope at or near a distal end of the insertion section. A positioning member is articulatively coupled to the base by an articulation link member. The positioning member has a channel disposed along a second longitudinal axis and in communication with a first and a second opening. The second opening of the positioning member is oriented toward a space exterior to the distal aperture of the holding member. The second longitudinal axis of the positioning member is moveable relative to the holding member first longitudinal axis.

In another embodiment, the endoscopic surgical access device according to the invention comprises an accessory channel member, a support body, a main body, and an actuator. The accessory channel member has first and second ends and a lumen. The support body has a guide portion and a base, whereby the guide portion has proximal and distal openings defining a passageway configured to slidably receive a portion of the accessory channel member, while the base has an abutting face intermediate a pair of projections. The main body has a coupler that articulatively joins the second body to the first body. The actuator is located at or near the main body and is configured to articulate the second body relative to the first body.

Methods of orienting endoscopic surgical access devices are also provided. In one embodiment, a method according to the invention comprises providing an articulating main body having a stationary first body, an articulatable second body, and a coupler articulatively joining the second body to the first body. The first body is detachably engaged to a distal end portion of an endoscope insertion section. The second body is articulated in at least one degree of freedom relative to the first body.

In another embodiment, a method according to the invention comprises providing an articulating main body having an accessory channel member received in a positioning member that has first and second ends and defining a passageway. Also provided is a support member having proximal and distal ends and defining a passageway. An accessory channel member is slid through the support member passageway. The articulating main body is attached to the distal end of an endoscope insertion section, and the device is placed endoscopically into a patient.

BRIEF DESCRIPTION OF THE DRAWINGS

FIG. 2B is an end view of a holding member used with a support member or an articulating main body in accordance with one embodiment of the invention.

FIG. 2C is an end view of an alternative embodiment of FIG. 2B.

FIG. 2D is an end view of an alternative embodiment of a holding member used with one embodiment of an articulating main body in accordance with the invention.

FIG. 2E is an end view of an alternative embodiment of FIG. 2D.

FIG. 2F is an end view of an alternative embodiment of FIG. 2D.

FIG. 3A provides a perspective partial view of a medical device according to a one degree of rotational freedom embodiment of the invention.

FIG. 3C is a perspective partial view of another embodiment of FIG. 3A.

FIG. 4A is a schematic perspective view of a articulating main body gimbal showing two rotational degrees of freedom.

FIG. 4B is an alternative embodiment of FIG. 4A showing two degrees of rotational freedom and two degrees of translational freedom.

FIG. 5A is an exploded perspective partial view of a medical device according to a multiple rotational degree of freedom embodiment of the invention.

FIG. 5B is an alternative embodiment of FIG. 5A showing multiple degrees of rotational freedom and two degrees of translational freedom.

FIG. 8A is a schematic side view of an alternative actuator embodiment having a double acting pneumatic (or hydraulic) cylinder actuator.

FIG. 8B is a schematic side view of an alternative actuator embodiment having a single acting pneumatic (or hydraulic) cylinder with a return spring in a relaxed state.

FIG. 8C is a schematic side view of FIG. 8B with a return spring in a pressured state.

DETAILED DESCRIPTION OF THE EMBODIMENTS

The present invention relates to medical devices and, in particular, to endoscopic surgical access devices and methods of positioning and/or orienting a tool at various angles with respect to the viewing field of an endoscope so that a physician, operator, or healthcare provider may maneuver the position and/or orientation of a tool within the visual field of the endoscope. For the purposes of promoting an understanding of the principles of the invention, the following provides a detailed description of several embodiments of the invention as illustrated by the drawings as well as the language used herein to describe the aspects of the invention. The description is not intended to limit the invention in any manner, but rather serves to enable those skilled in the art to make and use the invention. As used herein the terms comprise(s), include(s), having, has, with, contain(s) and variants thereof are intended to be open ended transitional phrases, terms, or words that do not preclude the possibility of additional steps or structure.

Figure 1:
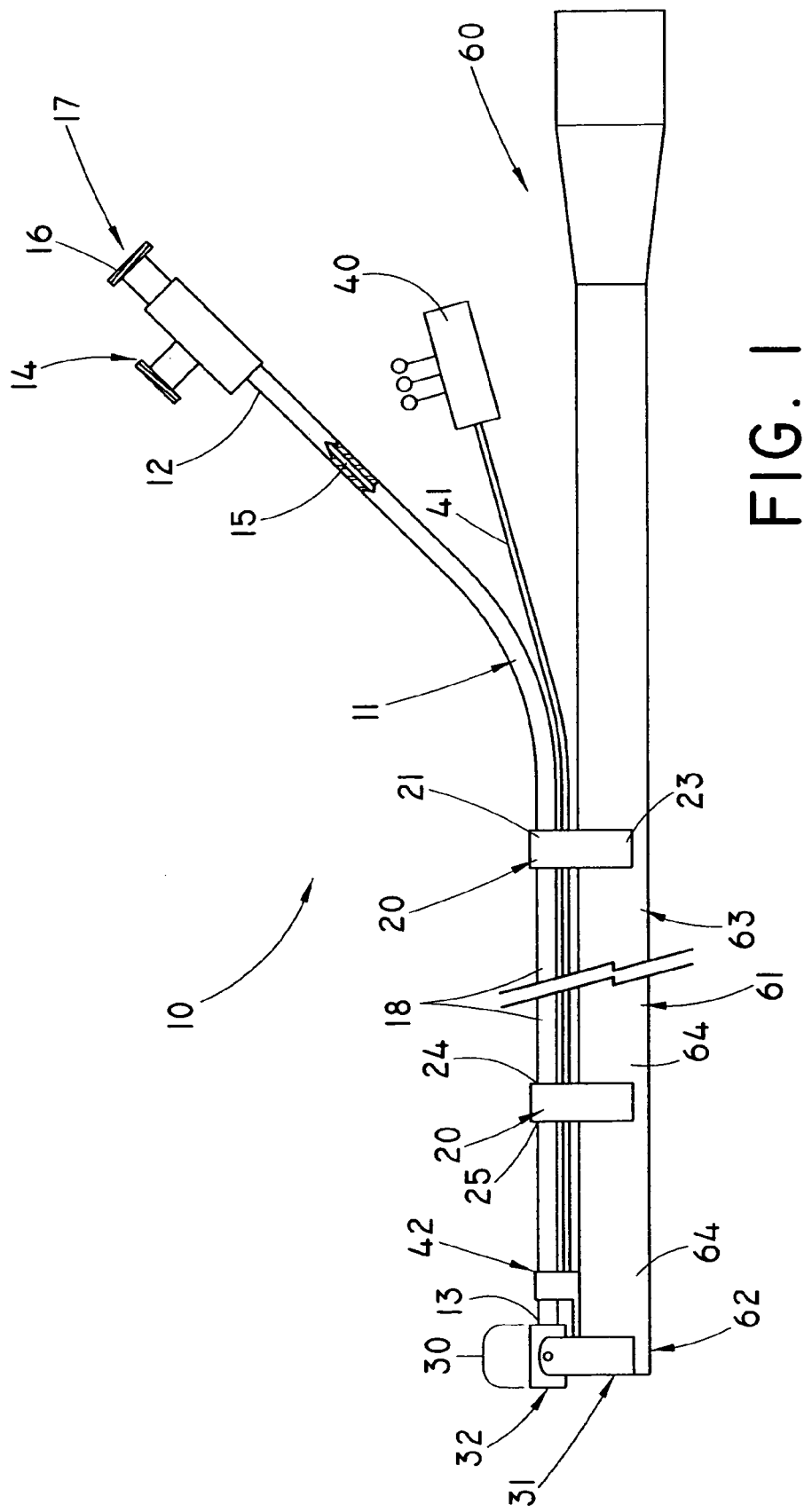
FIG. 1 is a side view, broken away, of a medical device according to one embodiment of the invention shown coupled to a schematic view of an endoscope.

As illustrated in FIG. 1, an endoscopic surgical access device containing various components of one embodiment of the present invention is provided. Device 10 is an embodiment of the present invention and comprises an accessory channel member 11, optional support members 20, and an articulating main body 30.

Accessory Channel Member

FIG. 1 illustrates an embodiment of the accessory channel member 11 through which, for example, diagnostic, monitoring, treatment, operating instruments, tools, and accessories (collectively, "tools") may be passed. The accessory channel member 11 may be generally tubular. As used herein to describe embodiments of the invention, the term "tubular" comprises any shaft, duct, vessel, tube-like structure, or elongated member with first 12 and second 13 ends that includes a lumen 15.

Given the common cylindrical configuration of tools and sheaths containing tools for endoscopic surgery, a nearly rounded or annular cross section of the channel member 11 may be better for passing the tool, having no corners or sharp angular obstructions for the tool to navigate. Thus, the cross-sectional profile of the channel member optionally may have circular or annular inner and outer diameters. As used herein in describing embodiments of the invention, "profile" means a cross-sectional profile. However, other profiles may be utilized, because the diameter of the tubular channel member need not be constant. Otherwise stated, the profile may vary along the length of the channel member in certain embodiments of the invention, as when the diameter of the channel member changes. Examples of other profiles of an accessory channel member, when viewed distally from the proximal end, include a profile that is tapered (reduced circumference), rounded, oblong, rectangular, ovulate, triangular, or a combination thereof as specific but non-limiting examples of accessory channel member embodiments that include a lumen for placing and axially sliding a tool.

In addition to varying in profile, the channel member 11 may vary in length given the different sizes of tools that may be passed through the channel. In certain embodiments of the invention, the channel member may be short and partially flexible, while in other embodiments the channel member may be long and flexible (e.g., bendable). Where long, flexible tubing is utilized for the accessory channel member, the tubing may be reinforced with braided stainless steel wiring, Kevlar, nylon, or other material so as to reduce the deformation that might result during bending, flexing, and stretching, which could affect and hinder ease of movement of the tool, result in occlusion of the lumen, or otherwise jeopardize the structural integrity of the channel member.

The accessory channel member 11 may be made of any suitable material (natural, synthetic, plastic, rubber, metal, or combination thereof). Thus, in general, the material may comprise a synthetic material that may include, for example, polyurethane, cellulose acetate, cellulose nitrate, silicone, polyethylene teraphthalate, polyamide, polyester, polyorthoester, polyanhydride, polyether sulfone, polycarbonate, polypropylene, high molecular weight polyethylene, polytetrafluoroethylene, or mixtures or copolymers thereof, polylactic acid, polyglycolic acid or copolymers thereof, a polyanhydride, polycaprolactone, polyhydroxy-butyrate valerate, polyhydroxyalkanoate, or another polymer or suitable material. Where it will not contact the patient (e.g., it is contained within a sheath), the channel member does not need to be biocompatible. In contrast, where there is the possibility of patient contact, then the channel member material may be biocompatible or capable of being made biocompatible, such as by coating, chemical treatment, or the like.

The channel member may be strong and resilient. The channel member may also be single or multi-layer, and may be composed of or include any material that is flexible, bendable, pliable, elastic, and stretchable (collectively, "flexible"). In certain embodiments of the invention, the channel member may be flexible in sections while rigid in other sections. For instance, the channel member may be flexible at or near its second end 13 and flexible at the first end 12, while having a more rigid intermediate section 18 intermediate the first and second ends 12, 13, respectively. Conversely, the channel member might have a rigid first end 12 while being flexible at its second end 13 and/or the intermediate section 18. In still a further embodiment, the channel member is flexible along its full length, including the first end 12, second end 13, and intermediate section 18. Other combinations of flexibility and rigidity can be imagined consistent with the invention described herein.

Figure 2A:
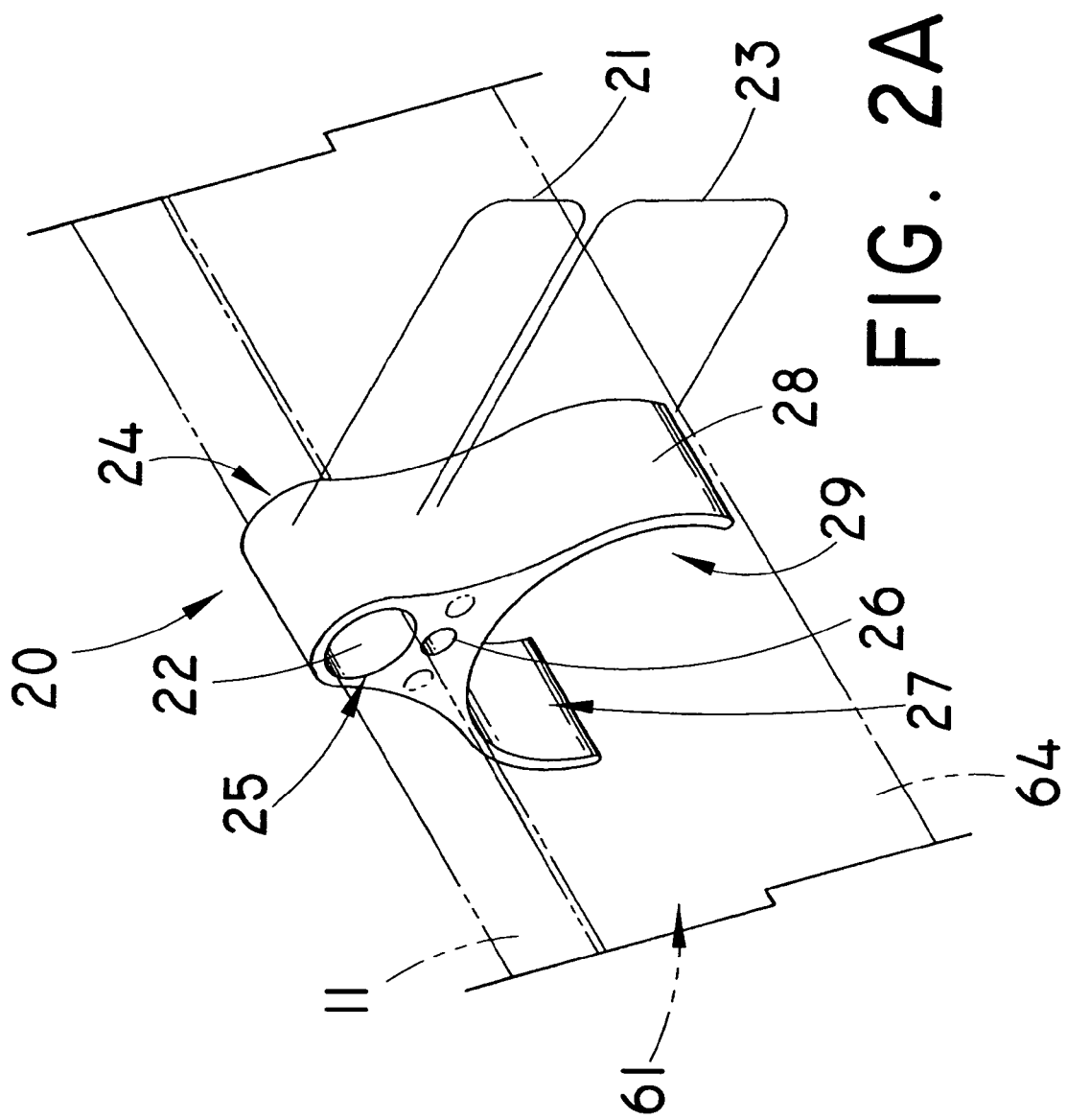
FIG. 2A is a perspective view of a support member.

As shown in FIGS. 1 and 2A, a long, flexible accessory channel member 11 is disposed longitudinally along a periphery 64 (outer surface) of an insertion section 61 of an endoscope 60 or other accessory such as a sheath enclosing the endoscope insertion section. For reference purposes and ease of discussion of the embodiments of the invention, the terms "insert" and variants thereof shall include the insertion section 61 of the endoscope that is inserted into the body together with and including any accessory that encloses or covers same, such as a sheath for example. In addition, the term "longitudinally" and its variants are intended to mean running lengthwise in a broad sense. However, it should be understood that the term "longitudinal" does not need to be straight—it could be curved as in a tangent to a referenced segment or point on or contained within an insert, because the accessory channel member 11 and insert 61 may be flexible, in which case "longitudinal" may be straight at some portions and bent at other portions along the length of, for instance, the insert.

The first end 12 of the accessory channel member 11 may be secured to an optional accessory channel adapter 14 as shown schematically in FIG. 1. The adapter further comprises an opening 16 and a lumen 17 for receiving a tool that is inserted axially within the accessory channel member lumen 15. The second end 13 of the accessory channel member 11 is secured to an articulating main body 30 (discussed below), where the term "secured" in describing embodiments includes articulatably, slidably, stretchably, or fixedly.

Support Member

As shown in FIG. 2A, the device optionally includes one or more support members 20. Where the accessory channel member 11 is short and stiff, a support member 20 may be unnecessary. However, the preference for one or more support members 20 increases with a long and flexible channel member 11 embodiment or a channel member 11 that is to be used with a long, flexible endoscope tube 60 and/or insert 61.

While the articulating main body 30 illustrated schematically in FIG. 1 detachably secures the second end 13 of the accessory channel member 11 to a distal end portion 62 of the insert 61, the channel member 11 may include optional support members 20 to provide support of the channel member 11 to the endoscope insert 61 intermediate the distal end portion 62 and proximal end portion 63 of the endoscope 60. As is conventional, "distal" means away from the physician, operator, or other healthcare professional ("physician") when the device is inserted into a patient, while "proximal" means closest to or toward the physician when the device is inserted into a patient. The term "intermediate" is intended to mean between the distal and proximal tips of the insert. Furthermore, the term "intermediate" is for the convenience of the reader, and could be considered to be a position at or near the distal end portion 62 or the proximal end portion 63 of the insert 61, and not necessarily equidistant to, or in the middle of, the distal and proximal end portions 62, 63, respectively. In addition, more than one support member 20 may be spaced as needed at various intervals longitudinally along the insert 61 and the accessory channel member 11.

Against the foregoing backdrop, a support member 20 is generally adapted to be capable of bridging the accessory channel member 11 to the insert 61. As illustrated in FIG. 2A, the support member 20 includes a guide portion 21 and a base 23.

The guide portion 21 has a passageway 22 configured for slidably (or fixedly) receiving another component such as the accessory channel member 11. As used herein, the term "passageway" is understood and used throughout to be any lumen, chamber, channel, opening, bore, aperture, orifice, flow passage, passageway, or cavity configured to facilitate the conveyance, flow, movement, stretching, holding, or sliding of the other component, such as an accessory channel member, sheath, cannula, tubing, tool as previously described, and the like (collectively, "component"). The passageway 22 is in communication with proximal and distal openings 24, 25, respectively, of the guide portion 21, and may be enclosed or may be cutaway (partially enclosed—as a ringed structure with a section removed therefrom). In the case of a slidable support, the inner diameter of the passageway 22 is larger than the outer diameter of the component such as the accessory channel member 11. If it is preferred that the component not be free to move (i.e., slidable) within the passageway 22 (as when, for example, an accessory channel member 11 is stretchable), then the diameters may be adapted such that the component fits snugly within the guide portion passageway 22. In the case of a stretching accessory channel member 11, the channel member may be constrained snuggly by the guide portion 21 of the support member 22 and the articulating main body 30 (or another support member 20) and may stretch therebetween as a result of an arcuate bending or flexing of the insert 61.

The guide portion 21 of the optional support member 20 may also have an optional auxiliary lumen 26 configured to receive a connector 41 that connects a remote controller 40 to the actuator 42 located at or near the articulating main body 30 (explained below). A single auxiliary lumen 26 may be positioned centrally or laterally as illustrated in FIG. 2A, and the support member may have more than one auxiliary lumen 26 as in FIGS. 2A, 2E, and 2F. Alternatively, the auxiliary lumen may be located at the base 23 of the support member 20.

The base 23 of the support member 20 is configured to serve as a structure that detachably engages a section of the support member to a section of the insert 61. The base 23 has an abutting face 27 serving as a structure that directly receives, touches, or otherwise contacts the insert 61 where, as previously explained, the term "insert" includes the insertion section 61 of an endoscope 60 as well as any accessory that encloses or covers a portion of same, such as a sheath. For example, the abutting face 27 of the base 23 may contact the periphery 64 (outer surface) of the insert 61 or of the insert containing device such as a sheath. The abutting face 27 may form a groove, arch, curve, or arcuate bridge (collectively, "curve," "curved," or variants thereof) as shown in FIG. 2A. Furthermore, the base 23 has at least one projection 28 defining an insert receiving cavity 29. The projection 28 is adapted for gripping the insert, as where a curved section of the abutting face 27 is locatable intermediate two projections 28 that straddle the curved section of the abutting face 27 as shown in FIG. 2A. Furthermore, the abutting face 27, which touches the insert, may be ribbed, have a rubber coating, or have an adhesive layer so as to increase friction. In bases with or without projections, and with or without ribs, rubber or adhesive coating, strap, tie, medical grade tape or adhesives may also be used if preferred by the operator for attaching the support member to the insert.

In one embodiment of the invention, a projection 28 is any suitable symmetric or asymmetric structure(s) forming an insert receiving cavity 29 configured for receiving a section of the endoscope insertion section and adapted to be capable of clamping, clutching, gripping, pinching, fastening, hooking, joining, or otherwise holding (collectively, "clips," "clipping," and variants thereof) the periphery 64 (outer surface) of the insert 61. FIGS. 2A, 2B, and 2C show variations of the clips at least partially encapsulating the insert, such as a ring structure with a segment removed therefrom. The base 23 structures depicted in FIGS. 2A, 2B, and 2C may be used with the support members 20 as well as with the articulating main body 30 (discussed below). In addition, the articulating main body 30 may utilize a base 23 structure shown in FIGS. 2D, 2E, and 2F, where the clip encapsulates the insert such as a ringed-shape structure 55 (a "ring clip" or sometimes called an "end cap"), or where the clip partially encapsulates the insert by removing the section shown in phantom in FIGS. 2E and 2F. FIG. 2E shows an alternative embodiment 110 having a base 23' and a guide portion 21' with multiple passageways 22 generally aligned in the same plane, while the embodiment 111 of FIG. 2F has a base 23", a guide portion 21", and multiple passageways 22 spaced apart. Base clips and a ring clip, as shown and described above, are two examples of holding members that detachably engage an insertion section and/or the distal end portion of an endoscope.

The foregoing designs for the base 23 of the support member may be incorporated into the articulating main body for holding the articulating main body to the distal end 62 of the insert, as discussed next.

Articulating Main Body

Figure 3:
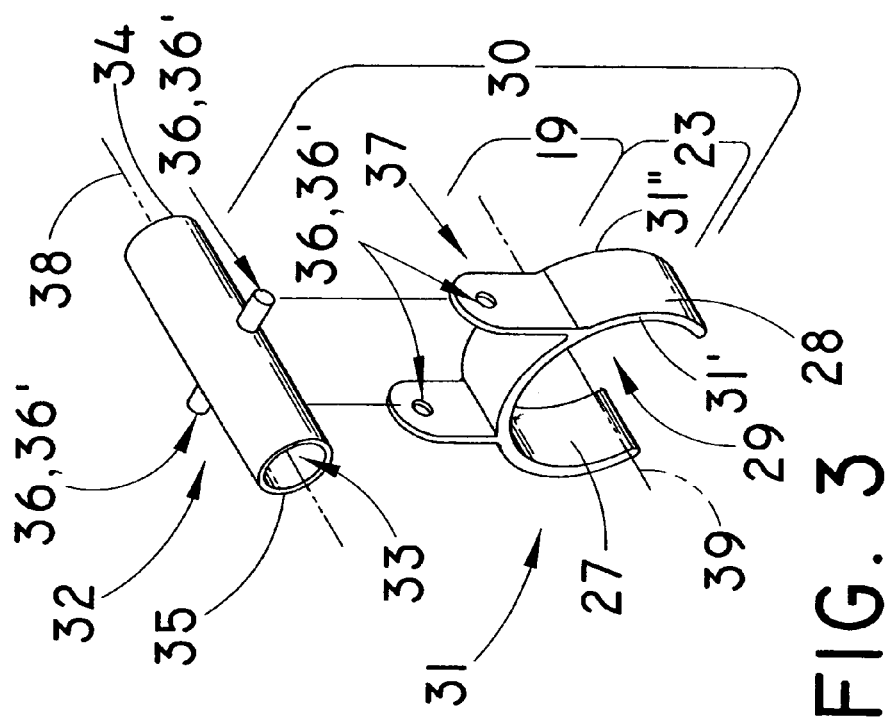
FIG. 3 provides a perspective view of an articulating main body according to an embodiment of the invention.

As shown in FIG. 3, the articulating main body 30 comprises a first body 31 and a second body 32 articulatively coupled thereto by a coupler 19.

Here, articulate means moveable and includes all degrees of translational displacements and/or rotations. For instance, the articulation may be axial, longitudinal, forward, backward, orthogonal, lateral, transverse, rotational, pivotable, sloping incline or decline, swinging, torsional, revolving, and other forms of translation and/or rotation in an x, y, and/or z coordinate system (collectively, "articulation," "articulate," "articulatable," "articulatively," and variants thereof).

Articulation occurs with respect to an articulation frame of reference. Articulation frame of reference includes any axis, joint, ball, bearing, pivot point, fulcrum, lever, hinge, real or imaginary line or reference point about which there is a translational and/or rotational range of movement (collectively, "frame of reference" or "articulation frame of reference"). For example, the articulation frame of reference in a one degree of rotational freedom system may be an axis, while the articulation frame of reference in a multiple rotational freedom system may be a reference point within a ball and axes therethrough.

The first body 31 is adapted to communicatively (e.g., indirectly) join the articulating second body 32 to a distal end portion 62 of an insert 61. The first body 31 has a distal end 31', a proximal end 31", and a holding member 23. The holding member is any suitable base 23 as previously described with respect to FIGS. 2A through 2F for detachably engaging the distal end portion 62 of an insert 61.

As such, the holding member 23 includes at least one insert clipping projection 28 (hereinafter, "projection 28," "projections 28," and/or "insert clipping projection 28") defining an insert receiving cavity 29 (hereinafter, "cavity 29" and/or "insert receiving cavity 29") having a first longitudinal axis 39 and an insert abutting face 27 (hereinafter, "abutting face 27" and/or "insert abutting face 27"). Holding members of the type that are partially encapsulating, as with projections 28 forming "clips" as shown in FIGS. 2A, 2B, and 2C resemble cantilevers, such as legs, sandwiching each side of the insert. Here, the term "side" is used to include, without limitation, even a periphery of a cylinder or the outside of any annular sheath or insert that has a substantially tubular periphery, such as the insert periphery 64. In other words, the sandwiching legs of the projections 23 exert vise-like force against opposing sides of the insert in order to hold the first body 31 to the insert distal end portion 62. Alternative shapes for holding members 23 comprising projections 28, an insert abutting face 27, and an insert receiving cavity 29 include saddle, U-shaped, or Omega-shaped (horseshoe-shaped) clip designs that snap onto and hold the distal end portion 62 of the insert 61. So that the projections 28 may snap over the insert 61 at the distal end portion 62, they optionally may be sufficiently pliable with an elastic memory. Also, as shown in FIG. 2B, the projections 28 may have reverse projections 53, 54 that facilitate clipping onto the insert by either providing a ramping effect, or facilitate clipping should the composition of the projections 28 be resistant to expansion. Holding members 23 of the type that include projections 28 that are encapsulating as with "ring clips" depicted in FIG. 2D-2F or that are partially encapsulated as in FIG. 2A, 2B, 2C, may have an inner diameter 50 that is smaller than the outer diameter 51 of the insert 61 or the distal end portion 62 of the insert in order to form a friction fit.

The insert clipping projection 28 detachably engages an insert 61 at or near a distal end portion 62 of an insert 61. By the phrase "at or near," it is meant that the insert clipping projection 28 may engage the distal end portion 62 of the insert 61 such that they are co-planar or offset. The term "offset" means that the distal end 31' of the first body 31 does not lie in the same plane as the distal face of the distal end portion 62 of the insert 61. In other words, the distal end 31' may be retracted from, or extending beyond, the distal end portion 62 of the insert 61.

Once the holding member 23 detachably engages the distal end portion 62 of the insert 61, the first body longitudinal axis 39 may be co-axial, parallel, or fixedly related to the distal end portion of the insert. In other words, the holding member 23 may detachably engage the insert distal end portion 62 such that the holding member 23 and insert distal end portion 62 are concentric or coincident. Alternatively, the longitudinal axis 39 may be offset, but substantially parallel, with respect to the distal end portion 62 of the insert 61. Another alternative is where the longitudinal axis 39 of the holding member 23 and the longitudinal axis of the distal end portion 62 of the insert 61 are fixedly related such that they extend in either the same (converge) or different (diverge) directions; in other words their angular relationship is substantially set but not parallel. In these alternatives, the first body 31 is said to be stationary, meaning that the first body 31 does not articulate independently of the distal end portion 62 of the insert 61. That is to say, where the axis of the distal end portion 62 of the insert 61 is translated and/or rotated within a frame of reference relative to the main body 30, then the holding member 23 of the articulating main body 30 substantially makes a concomitant translation and/or rotation.

The second body 32 is generally adapted to be capable of articulating with respect to the first body 31. In one embodiment, the second body 32 may be the second end 13 of the accessory channel member 11 that couples to the first body 31 via a coupler 19 comprising at least one articulation link member 36 and a mounting member 37 (discussed below). In another embodiment, the second body 32 may be a plate to which the second end channel member is secured.

Another alternative embodiment of the second body 32 is a positioning member, which is a structure configured to be capable of articulating the second end 13 of the accessory channel member 11. In one embodiment, the positioning member is configured to slidably hold the second end 13 of the accessory channel member 11, such that there is a slip fit that allows the second end 13 of the channel member 11 to be slidable during articulation. In an alternative embodiment, the positioning member is capable of being made to bind or constrain a portion of the channel member second end 13 and, thereby, orient or reposition the second end 13 of the channel member 11 with respect to the viewing field of the distal end portion 62 of the insert 61.

Certain non-limiting examples of a second body 32 that is a positioning member include a fully circumferential or cutaway periphery of a cannula, tube, duct, vessel, or other tubular structure defining a passageway 33, as previously described, and sized to fixedly receive the second end 13 of the accessory channel member 11, which channel member second end 13 is fitted, inserted, nested, placed, or positioned axially within the passageway 33. The tubular positioning member may be secured to the second end 13 of the channel member 11 by friction, adhesive, glue, barbs, or any combination thereof, to name a few, or it may constrain the second end 13 of the accessory channel member 11 via a slip fit (collectively, "adapted").

Another example of binding the second end 13 of the channel member 11 is where second body 32 is a tubular positioning member (either enclosed or of the cutaway type), such that there is an accessory channel member side (e.g., the inside) and a second opposing side (e.g., outside), and a portion of the accessory side has an adhesive layer (e.g., glue) to hold the channel member. In lieu of or in addition to adhesives, friction may hold the channel member to a positioning member, as where, for instance, the tubular positioning member comprises a first portion having a first cross-sectional area and a second portion having a second cross-sectional area that is smaller than the first cross-sectional area. Another illustration of a friction fit is where the second body 32 is a tubular positioning member having a substantially cylindrical first portion and a second tapered portion. In these friction-fit examples, the second end 13 of the accessory channel member 11 is placed axially into the tubular positioning member passageway 33 (into a proximal opening 34 having a first cross-sectional area or being substantially cylindrical) and fits snugly as it moves axially within the tubular positioning member passageway 33 (toward a distal opening 35 having a smaller second cross-sectional area or being tapered).

As with the other features of the invention, the second body 32 that is a positioning member, as previously described, may be made of any suitable material (natural, synthetic, plastic, rubber, metal, ceramic, polymer, or combination thereof). Where there is the possibility of patient contact, then the positioning member may be comprised of a material that is biocompatible or capable of being made biocompatible, such as by coating, chemical treatment, or the like. Furthermore, the positioning member may be machined, cut, milled, extruded, molded, or formed by any suitable means, or it may even be integrally pre-formed to the second end 13 of the accessory channel member 11.

Also, the second body 32 includes a longitudinal axis 38. For example, the longitudinal axis 38 of a tubular positioning member is a substantially straight, fixed, or curved imaginary line that is symmetrical to, or bisects, the tubular positioning member. The longitudinal axis 38 of the second body 32 is moveable relative to the longitudinal axis 39 of the first body 31 or the distal end portion 62 of the insert 61. The second body 32 is generally configured to be adapted to the second end 13 of the accessory channel member 11, coupled to the first body 31 with articulation link members 36 and mounting members 37, and articulate in relation to the first body 31 such that the longitudinal axis 38 of the second body 32 is moveably associated with the first body 31 about an articulation frame of reference, such as the first body longitudinal axis 39.

Exit Trajectory

And now a word about the exit trajectory of a tool as used with embodiments of the invention. As a result of the foregoing discussion, it should be understood that the second body 32 and the first body 31 are coupled—via a coupler 19 comprising at least one articulation link member 36 and a mounting member 37 (discussed below)—such that the second body 32 may articulate with one or more degrees of rotational and/or translational freedom. An embodiment may have, for example, two degrees of rotational freedom and two translational degrees of freedom for a total of four degrees of freedom. A further example may have three rotational degrees of freedom and two translation degrees of freedom for a total of five degrees of freedom. Many combinations may be imagined and, thus, a system may have from one to many degrees of freedom.

Accordingly, a tool may be inserted into the accessory channel member lumen 15 and may exit or extend from a distal opening 35 of the second body 32. Because the second body 32 articulates within an articulation frame of reference (such as the first body longitudinal axis 39, for example) in rotational and/or translation degrees of freedom, the second body 32 may be maneuvered, positioned, and pointed in a way that controls the exiting trajectory of the tool or the position of a tool that is extending from the distal opening 35 of the second body 32. Thus, the physician may control the position and/or orientation of the tool within the endoscope observation field and working space by articulating the second body 32.

Articulation Link Member(s)

In rotational and/or translational degree of freedom systems, the second body is associated with the first body 31 by one or more couplers 19, which may be any structures or mechanisms configured to be capable of coupling the first and second bodies 31, 32, respectively, such that the second body 32 is in communication with—directly or indirectly via the coupler—the first body 31 and permitted to articulate relative to the first body 31, or the second longitudinal axis 38 moves relative to the first longitudinal axis 39. Therefore, the first and second bodies may be articulatively coupled via a coupler 19 comprising at least one articulation link member 36 and a mounting member 37.

Certain non-limiting examples of articulation link members 36 include any full or partial bearing, pin, shaft, thread, rod, bar, ball or hemispherical ball, fulcrum, joint, support, sprocket, wheel, protuberance, projection, protrusions, or other linkages (collectively, "articulation link member(s)"). It should be understood that articulation link members 36 may be chamfered, beveled, flat, pointed, rectangular, right circular cone, triangular, tubular, or rounded designs that facilitate articulation. Furthermore, it should be understood that an articulation link member 36 may take on various shapes that are consistent with a range of motion defining an articulation frame of reference.

An articulation link member 36 may be either on the first body 31, the second body 32, or a structure that couples the first and second bodies or may comprise a structure that couples a first and second body (i.e., allows the second body 32 to be in communication with—directly or indirectly via the articulation link member 36—the first body 31 articulatably). Where an articulation link member 36 is on the second body 32, for example, then the first body 31 may have one or more articulation link member receptors 36' designed to receive and articulatively retain the opposing body's articulation link members 36. Keeping with the example, if an articulation link member 36 is on the first body 31, then one or more articulation link member receptors 36' may be on the second body 32. There may be both articulation link members 36 and receptors 36' on each of the bodies 31, 32, respectively.

Non-limiting examples of articulation link member receptors 36' include but are not limited to slots, chambers, indents, dimples, recesses, holes, cutouts, cavities, or other contoured bearing surfaces. In addition, the receptors 36' and link members 36 may be coated or partially coated with a low friction material or lubricant such as polytetrafluorethylene to reduce friction between surfaces. Also, the receptors 36' and link members 36 may utilize any proper securing mechanism such as a nut, bolt, screw, thread, cotter and pin, or spring-biased.

Because there may be embodiments containing one, two, and three degrees of rotational freedom and/or one or more degrees of translational freedom, there may be more than one articulation link member 36 and receptor 36'. Also, the embodiments may have a corresponding or unequal number of link members 36 and receptors 36'. Reference numerals 36 and 36' in the drawings refer in general to an articulating link member and/or articulating link member receptor. Thus, where the drawing shows a 36 without a 36', then 36 may be an articulating link member or an articulating link member receptor.

One Degree of Freedom

One embodiment of an articulating main body 30 may utilize a one degree of freedom system. This may be translational or rotational. Examples of a translation one degree of freedom system includes an x-z table, where the second body 32 is displaced in either the x or z direction. Examples of a rotational one degree of freedom system include a pitch or a yaw system. With the first body 31 chosen as a reference, a yaw system allows side to side articulation of the second body 32 relative to the first body 31 about a yaw frame of reference (e.g., axis), while a pitch system allows upward or downward articulation of the second body 32 relative to the first body 31 about a pitch frame of reference (e.g., axis).

The second body 32 may be moveably mounted onto the first body 31 by articulation link members 36 (previously described) about a yaw or pitch articulation frame of reference. As used to describe embodiments of the invention disclosed herein and in the figures, the term "mounted onto" includes any arrangement whereby the second body 32 is moveably in communication with the first body 31 directly or indirectly via a coupler 19 comprising a mounting member 37 and an articulation link member 37. Certain non-limiting examples of mounting members 37 may include any suitable structure, such as a bracket, yoke, cradle, blocks, plates, or other male-to-female couplers that utilize one or more of the foregoing articulating link members 36 and receptors 36'. These mounting members 37 may also be considered to be articulating link members 36 as coupling the first and second bodies 31, 32, respectively. The mounting member 37 may be either on the first body 31, on the second body 32, or a structure on both so as to couple the first and second bodies 31, 32, respectively.

Figure 3B:
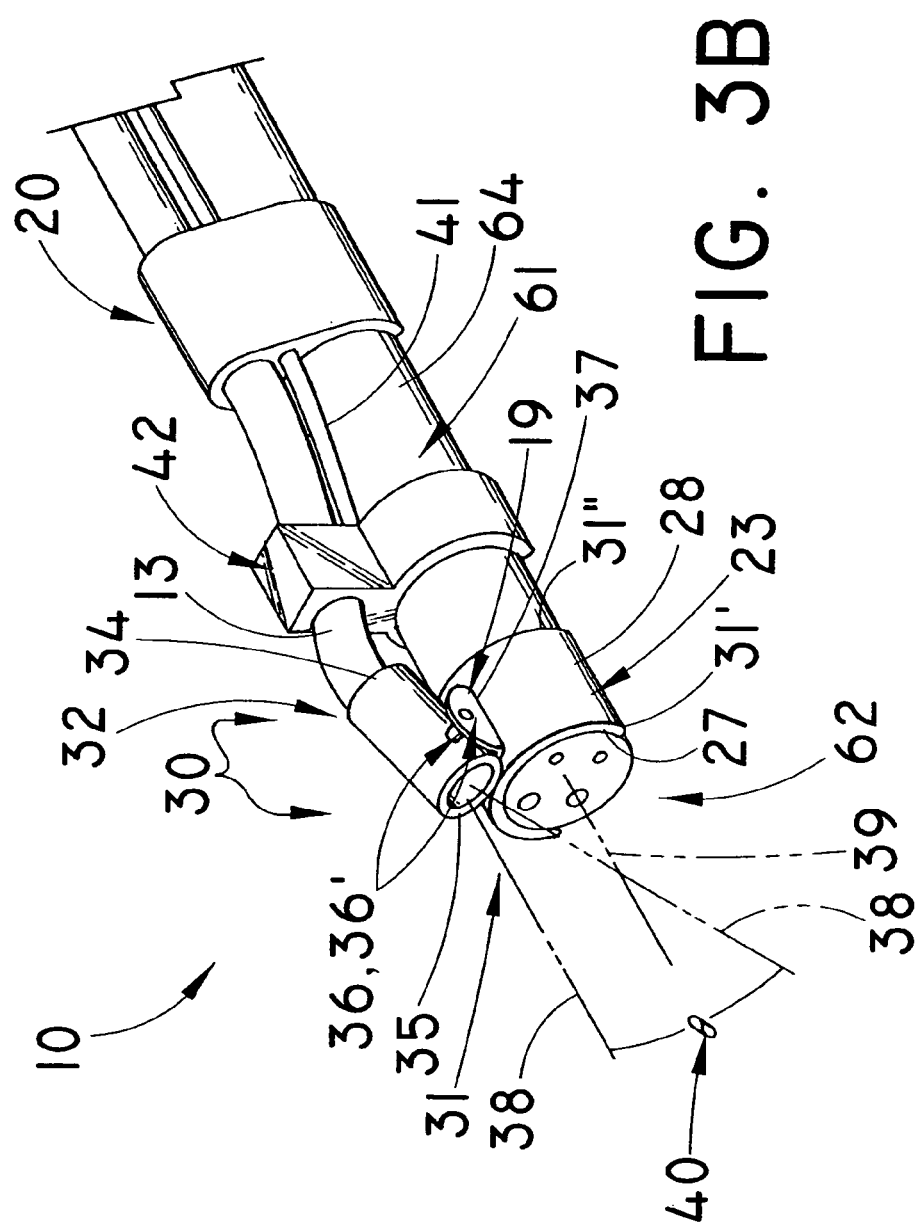
FIG. 3B is a perspective partial view of an alternative embodiment of FIG. 3A.

FIGS. 3A, 3B, and 3C show alternative embodiments of an articulating main body 30 utilizing a one degree of rotational freedom system. FIG. 3A illustrates a perspective partial view of a distal section of an embodiment 10 comprising an accessory channel member 11 having a second end 13 that is set longitudinally at or near the periphery 64 of the distal end portion 62 of the endoscope insert 61. Also shown is an optional support member 20 that is provided for bridging the accessory channel member 11 to the insert 61. The support member 20 includes, as previously described, a guide portion 21 having a proximal and distal opening 24, 25, respectively, defining a passageway 22 for receiving the accessory channel member 11, and a base 23 for detachably engaging the periphery 64 of the insert 61. The support member 20 of FIG. 3A also has an optional auxiliary lumen 26 configured to receive an optional connector 41, which as explained below may operably connect a controller 40 (not shown) to the actuator 42 (not shown) that is located at or near the articulating main body 30.

The articulating main body 30 comprises a first body 31, as previously described, for holding the main body 30 to the distal end portion 62 of the insert 61. In addition, a second body 32 secures the second end 13 of the accessory channel member 11, where the term "secured" in describing embodiments includes articulatably, slidably, stretchably, or fixedly. The second body 32, as previously described, has proximal and distal openings 34, 35, respectively, defining a passageway 33 and having the second end 13 of the accessory channel member 11 positioned axially within the second body passageway 33, intermediate the proximal and distal openings 34, 35, or extending externally distal to the distal opening 35. The distal opening 35 is oriented toward a space exterior to the first body holding member 23 (such as distal to the distal end 31' of the first body 31).

Two horizontal articulating link members 36 form a pitch articulation frame of reference and are shown approximately intermediate the proximal and distal openings 34, 35, respectively, of the second body 32 for articulatively coupling— directly or indirectly—the second body 32 to the first body 31 via mounting members 37 in FIGS. 3A, 3B, and 3C. The medial position of the link members 36 in FIGS. 3A and 3B permits rocking of the proximal and distal openings 34, 35, respectively, of the second body 32. Where the link members 36 are positioned medially as in FIGS. 3A and 3B, the permissible angle of articulation of the second body 32 to the first body 31 is limited by the height of the clearance between the first and second bodies 31, 32, respectively. In a yawing system, the mounting member 37 would serve to restrict the articulation of the second body 32 by the width or separation of the second body 32 to the mounting member 37 acting as yaw restraints.

FIG. 3B is an alternative embodiment of a one degree of rotational freedom system. Dashed lines illustrate the longitudinal axis 38 of the second body 32 and the longitudinal axis 39 of the first body 31 generally. The distal end portion 62 of the insert 61 occupies the insert receiving cavity 29 (not shown). In FIG. 3B, the longitudinal axis 39 is shown coaxial with the distal end portion 62 of the insert 61. The second body 32 distal opening 35 is oriented toward a space exterior to the distal end portion 62 of the insert 61 and the first body 31 at an angle of articulation 40 designated as theta in FIG. 3B. In addition, compared to FIG. 3A where the articulating main body 30 includes an actuator (not shown but optionally contained within the articulating main body 30 of FIG. 3A), in FIG. 3B the actuator 42 is shown as a separate component proximal to the articulating main body 30 and operated via an optional connector 41 from a remote controller 40 (not shown).

FIG. 3C is an alternate embodiment of a one degree of rotational freedom system of FIG. 3A. However, the two horizontal articulating link members 36 have been positioned distally to form a pitch axis at or near the distal end opening 35 of the second body. The second body 32 distal opening 35 is oriented toward a space exterior to the distal end portion 62 of the insert 61 and the first body 31 at an angle of articulation designated as alpha.

Two Degrees of Freedom

Another embodiment of the articulating main body 30 may utilize at least a two degree of freedom system. This may be translational, rotational, or a combination thereof. For instance, a one degree of translational freedom system (as in the x or z direction in an x-z table, discussed below) may be incorporated into FIG. 3A, 3B, or 3C and result in two total degrees of freedom. As a further non-limiting example discussed below, an embodiment may have two rotational and two translational degrees of freedom.

Examples of two degrees of rotational freedom include a pitch-yaw system, and one example of such a device is a gimbal. With the first body 31 chosen as a reference, a pitch-yaw system allows side to side articulation of the second body 32 relative to the first body about a yaw frame of reference, while also permitting upward or downward articulation of the second body relative to the first body about a pitch frame of reference.

FIG. 4A is a schematic view of an articulating main body 30 having a first body (not shown) and a second body 72, as first and second bodies have been previously described. The main body 70 utilizes a two-articulation frame of reference option such as a gimballing pitch-yaw system. A coupler 19 comprises mounting member 77 and an articulation link member 78 that articulate the second body 72 about a yaw frame of reference defined by articulation link member 78. The second body 72 also may articulate about the pitch frame of reference defined by articulation link member 76.

FIG. 4B is an alternative embodiment of FIG. 4A showing two degrees of rotational freedom and two degrees of translational freedom. The coupler 19 has an articulating link member 78 that fits into an x-z table. Here, the x-z table is illustrated as a translational plate 43, which is capable of being displaced in the x-direction and/or the z-direction. Consequently, when the translational plate is coupled to an articulation link member of a two degree of rotation system, the second body has two rotational degrees of freedom and may also be displaced in the x and/or z direction, for a total of four degrees of freedom.

Figure 4D:
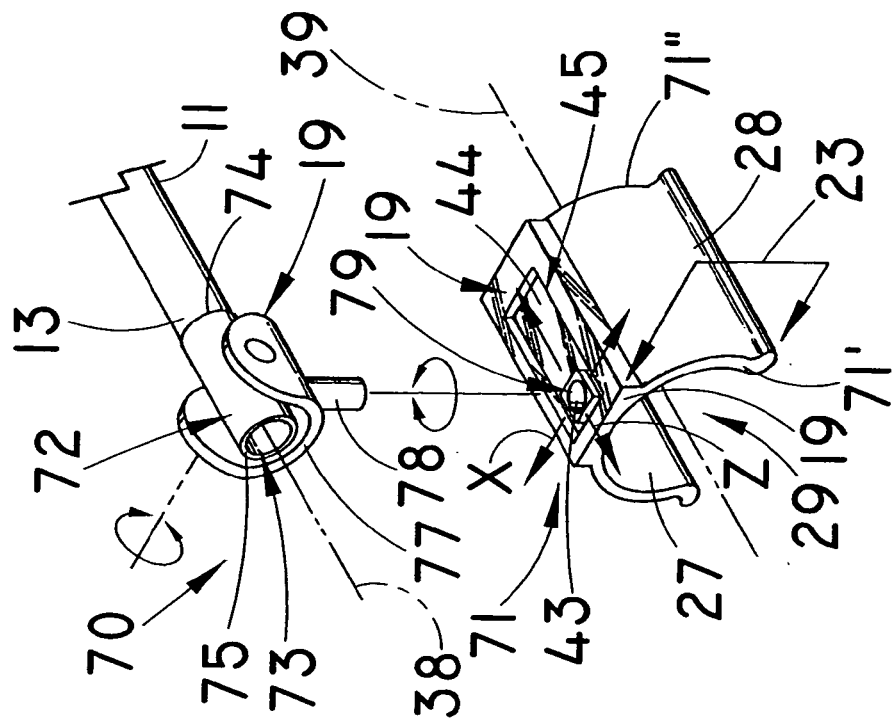
FIG. 4D is an alternative embodiment of FIG. 4C showing two degrees of rotational freedom and two degrees of translational freedom.
Figure 4C:
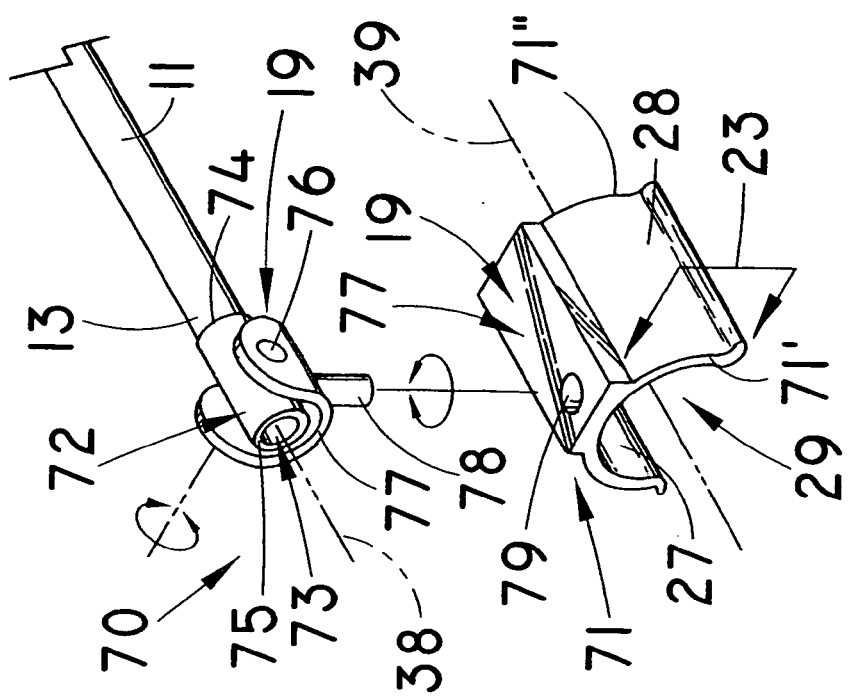
FIG. 4C is an exploded perspective partial view of a medical device according to a two degree of rotational freedom embodiment of the invention.

FIG. 4C shows an articulating main body 70 having a first body 71 and a second body 72 as previously described, and that utilizes a two degree of freedom system. FIG. 4C illustrates a perspective partially exploded view of a distal section of an embodiment with emphasis on the two degree articulating main body 70. Also depicted is a view of the second end 13 of an accessory channel member 11 positioned in a passageway 73 intermediate distal 75 and proximal openings 74 of the second body 72. The articulating main body 70 further comprises a first body 71 configured to detachably engage the distal end portion 62 of the insert 61 (not shown).

A coupler 19 includes horizontal articulating link members 76 that form a pitch frame of reference articulatively coupling the second body 72 to the first body 71 via a mounting member 77 and an articulation link member 78. Another coupler 19 comprises a vertical articulating link member 78 that forms a yaw frame of reference and is received in an articulation link member receptor 79 for articulatively coupling the mounting mechanism 77 to the first body 71.

Figure 4E:
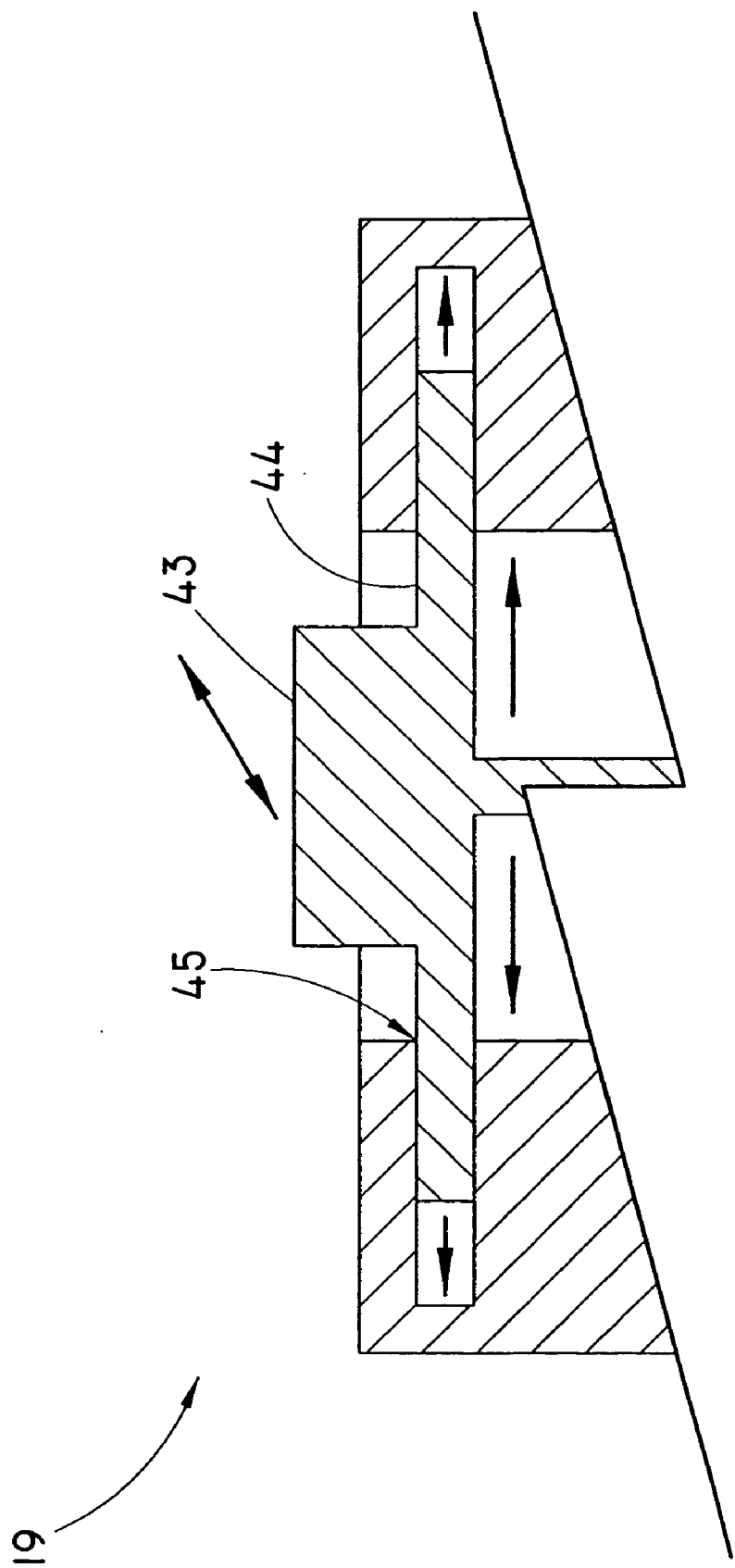
FIG. 4E is a schematic of a two degree of translational freedom embodiment.

FIG. 4D is an alternative embodiment of FIG. 4C showing two degrees of rotational freedom and two degrees of translational freedom. The articulating link member 78 fits into an articulation link member receptor 79 of x-z table illustrated as a translational plate 43. The translational plate 43 acts as a mounting member for fixedly or articulatively securing the articulating link member 78. The translation plate 43 comprises a flange 44 that interfaces with a first body flange receptor 45 to keep the translational plate 43 from lifting off. The translational plate is capable of being displaced in the x-direction and/or the z-direction via the flange 44 acting as an articulation link member received in the first body flange receptor 45 configured to allow articulation (here, of the translation type) of the flange 44 and, thereby, the translation plate 43. FIG. 4E is a schematic view of a two degree of translational freedom embodiment. When the translational plate 43 is coupled with the rotational articulation link members shown in FIG. 4D, the second body 72 has two rotational degrees of freedom and may also be displaced in the x and/or z direction, for a total of four degrees of freedom.

Multiple Degrees of Freedom

Another embodiment of the articulating main body 80 may utilize at least a multiple degree of freedom system. This may be translational, rotational, or a combination thereof. One example of a multi-degree of rotational freedom system includes a pitch-yaw-roll system, while another example comprises a ball-and-socket system.

FIG. 5A is a perspective partially exploded view of an articulating main body 80 that illustrates a distal end portion of an embodiment with emphasis on an articulating main body 80 that utilizes a multi-degree of rotational freedom system comprising first and second bodies 81, 82, respectively, operatively adapted to be joined—indirectly one to another—via a coupler 19 that is a ball-and-socket joint arrangement.

The ball-and-socket joint arrangement has an articulating link member that comprises a ball portion 83 protruding from a region of the first body 81 and also having a corresponding articulating link member receptor that comprises a socket portion 86 located in the adjoining second body 82. Although the ball portion 83 and socket portion 86 in FIG. 5A are shown on the first and second body 81, 82 respectively, these relative positions may be interchangeable, by placing the ball portion 83 on the second body 82 and the socket portion 86 on the first body 81.

In FIG. 5A, the ball portion 83 has a knob 85 supported on a stem 84, and the socket portion 86 has a socket 87 that articulatively receives the knob 85. In one embodiment of the ball-socket joint arrangement, the socket portion 87 is provided with a contoured cavity arrangement having the socket in its interior.

The dashed lines in this exploded FIG. 5A illustrate the range of motion illustrated by reference numeral 88 of the second body 82 about an articulation frame of reference of the ball 83, but it should be understood that the articulation frame of reference could be drawn with respect to the socket portion 87. FIG. 5A also shows a second body longitudinal axis 89 corresponding either to an exit trajectory in the neutral position, or with respect to the longitudinal axis 39 of the first body 81, or with respect to the distal end portion 62 of the insert 61.

A contoured cavity arrangement formed in the socket portion 86 may be utilized to delimit the desired extent of articulation of the stem 84. This limitation of movement is achieved because the socket portion 86 has side walls 98 that determine the extent of movement for the stem 84 within the socket 87. In other words, as the second body 82 articulates about the knob (ball) 85, the stem 84 bumps up against the side walls 98 of the socket portion 86. Using this principal, a socket portion 86 having distal and proximal arcuate cutouts will have greater pitch movement, and yaw articulation may be limited by lateral side walls. Conversely, a socket portion 86 having arcuate lateral cutouts but distal/proximal side walls would have a greater degree of freedom of articulation generally in the yaw direction than in a pitch direction. Furthermore, if a socket portion 86 has short side walls that come down just slightly south of the equator (figuratively) of the knob 85, then this socket portion 86 will allow a greater degree of articuluation in the pitch, yaw, and roll directions that it would with longer side walls.

FIG. 5B is an alternative embodiment of FIG. 5A further showing two potential degrees of translational freedom. The stem 84 fits to a translational plate 43, which is capable of being displaced in the x-direction and/or the z-direction. It should be understood that the translational plate 43 may have a flange 44 that interfaces with a first body flange 45 to keep the translational plate from lifting off, as previously illustrated and described in the context of FIG. 4D. Therefore, the second body 82 has multi-rotational and two translational degrees of freedom.

Controller, Connector, and Actuator

FIG. 1 schematically illustrates a controller 40. The controller may be part of the device 10, may diverge and be detachable (separable) from the device 10, may be attached to the accessory channel adapter 14 with support members 20, or the controller may be a wireless remote control. The controller 40 is located within reach of the physician, operator, or healthcare professional, and typically (though not necessarily) may be located at the proximal first end 12 of the device 10. The controller 40 remotely, selectively, and communicatively regulates one or more actuators 42, 90, 90' for one or more of each degree of freedom, which actuator is located (but not shown in FIG. 1) at or near the articulating main body 30 of the device 10 via a connector 41, except in the case of a wireless controller which does not need a connector 41.

The controller 40 may be a mechanical handle to move a wire or cable, a hydraulic handle to regulate water or other liquids to move pistons and cylinders, a pneumatic input/output to regulate the flow of air or other gases (pneumatic), or one or more electrical switches. Extending distally from the controller 40 is the connector 41 (except in the case of a wireless remote controller). The connector 41 is a mechanism (e.g., an elongated mechanical wire, rod, shaft, cable and sheath; an elongated pneumatic tube or hydraulic flow paths, or an electrical conductor) capable of extending at or near the controller 40 to one or more actuators 42, 90, 90' located at or near the articulating main body 30. The connector 41 may be housed in a suitable tubular structure.

Figure 6A:
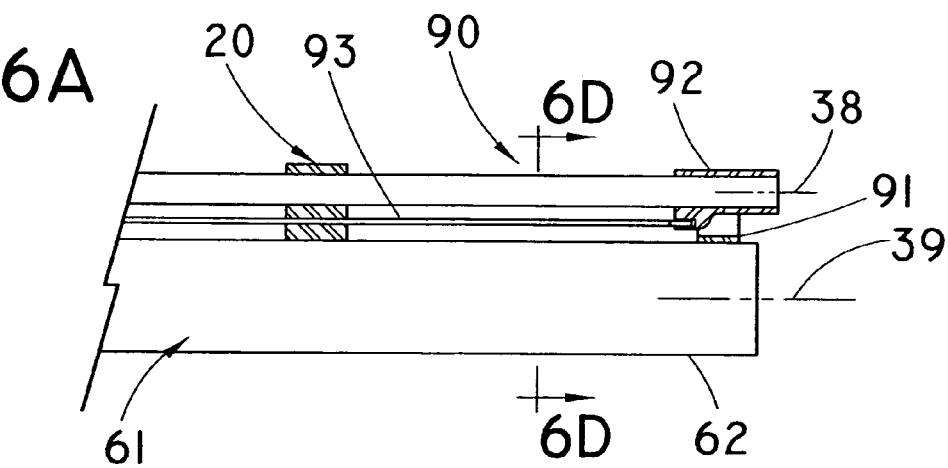
FIGS. 6A through 6C are sectional side views during actuation of an actuator embodiment having a crank actuator to facilitate articulation.
Figure 6B:
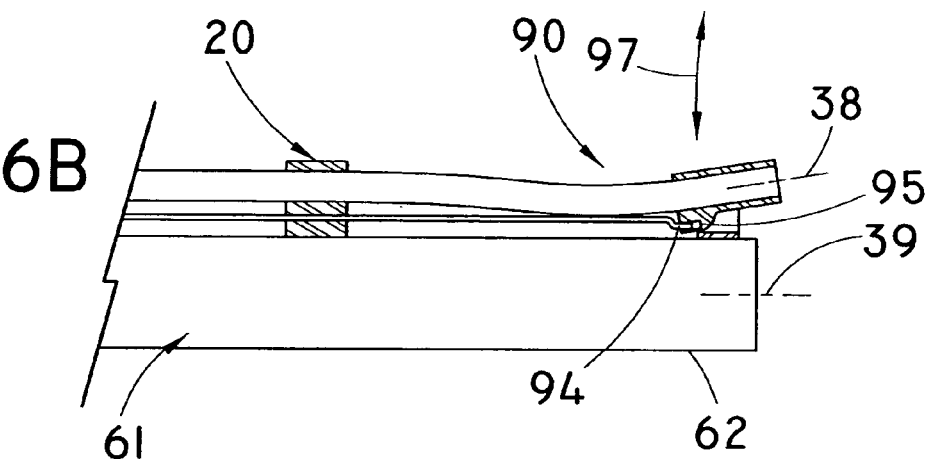
Figure 6C:
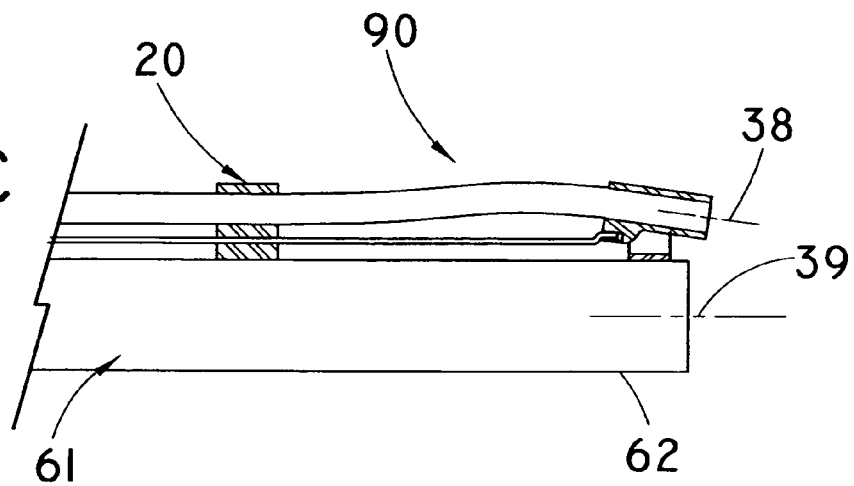

FIGS. 6A, 6B, and 6C are sectional side views that schematically illustrate an embodiment of an actuator 90 during actuation. As shown, one possible embodiment of an actuator 90 is a rotation shaft 93 (e.g., a crank) that facilitates the articulation (e.g., in the directions of the double-headed arrow 97 in FIG. 6B) of the second body 92 relative to the first body 91. The crank adjusts the angle of the second body 92 and, thus, controls the position and/or orientation of the tool that may exit or extend from a distal opening at the distal end of the second body 92 by rotating the crank end offset 94 (see FIG. 6B) captured within a slot 95 in the second body 92.

Figure 6F:
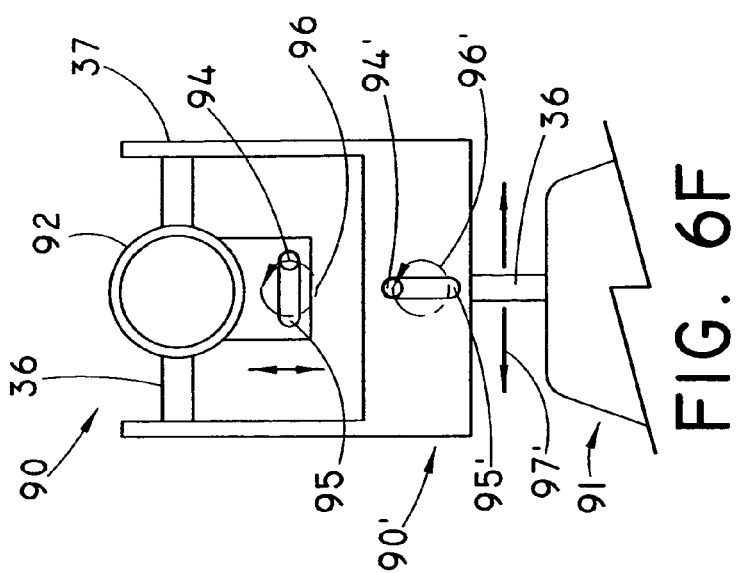
FIG. 6F is a sectional end view of a two-actuator embodiment incorporating the actuator of FIG. 6D and an alternate version of the actuator of FIG. 6D containing a vertical slot.
Figure 6E:
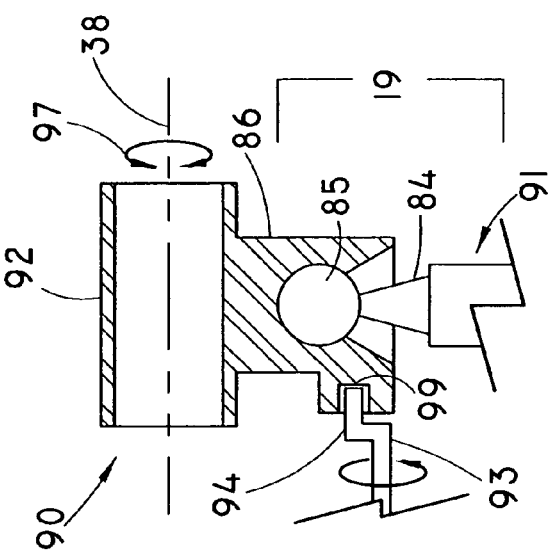
FIG. 6E is a sectional side view of an alternative actuator embodiment having a crank actuator to facilitate articulation about a multi-degree of freedom ball and socket.
Figure 6D:
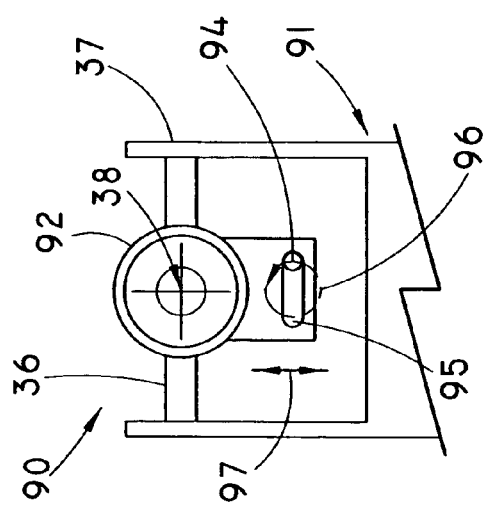
FIG. 6D is a sectional view of FIG. 6A along the line 6D-6D.

FIG. 6D is a sectional view of FIG. 6A along the line 6D-6D. It illustrates the circular rotation 96 of the offset end 94 of the rotation shaft 93, whereby the offset end 94 moves in the actuation slot 95 and articulates (e.g., in the directions of the double-headed arrow 97) the second body 92 longitudinal axis 38 both directions vertically. FIG. 6E is a sectional side view of an actuator 90 in a three degree of freedom articulation embodiment of the invention (e.g., in a circular 360 degree rotation in the directions of the double-headed arrow 97) by adapting the crank mechanism using a ball 85 and socket 86 assembly. This movement is generated by containing the crank offset end 94 in a hole 99, rather a slot. These are just a few examples of mechanical actuators to facilitate articulation about one degree of freedom axis or multi-degree of freedom ball and socket. It should be understood that the mechanical actuators may actuated by electricity, making themn electromechanical actuators.

FIG. 6F is a sectional end view of a two-actuator 90, 90' embodiment incorporating the actuator 90 of FIG. 6D and an alternate version of the actuator 90' of FIG. 6D containing a vertical slot. In FIG. 6F, a first actuator 90 includes a crank end offset 94 captured within a horizontal slot 95 in the second body 92 and moved about a circular rotation 96 to articulate the second body 92 about a pitch frame of reference. A second actuator 90' includes a crank end offset 94' captured within a vertical slot 95' in the first body 91 and moved about a circular rotation 96' to articulate the second body 92 about a yaw frame of reference.

Figure 7B:
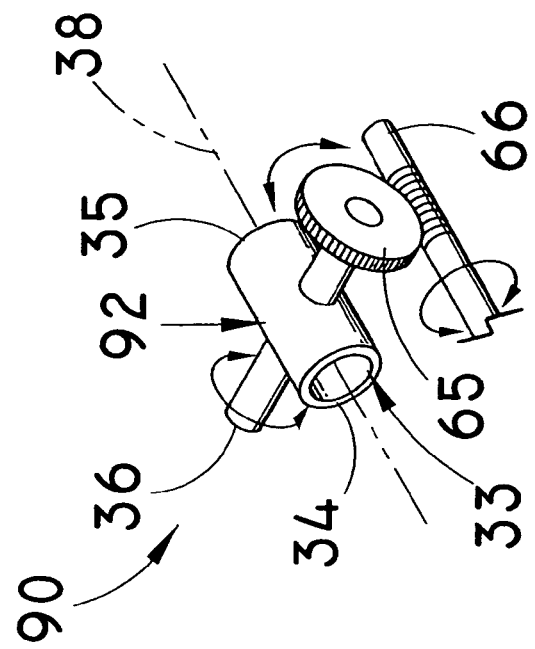
FIG. 7B is a perspective view of an alternative embodiment of FIG. 7A.
Figure 7A:
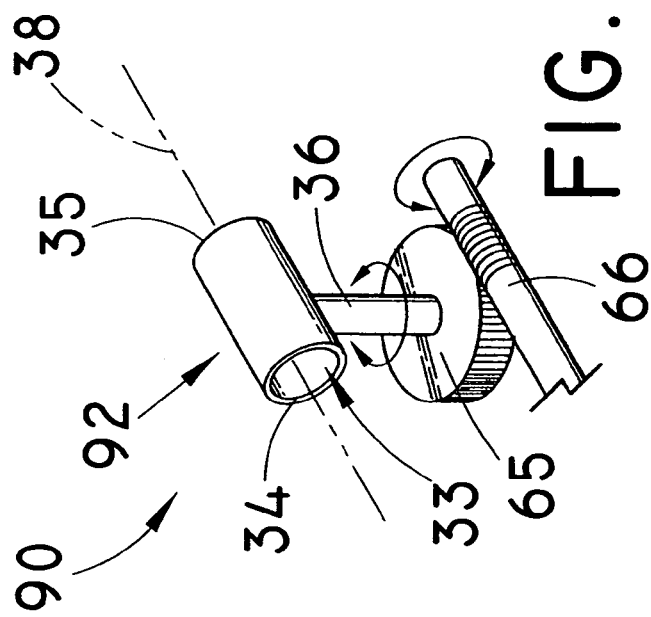
FIG. 7A is a sectional perspective view of an alternative actuator embodiment having a pinion and gear actuator.

FIG. 7A illustrates an actuator 90 comprising a pinion 66 and a gear 65 to facilitate rotation of the second body 92 about a vertical (yaw) frame of reference, such as the articulating link member 36. In contrast to the horizontal gear 65 of FIG. 7A, the actuator 90 in FIG. 7B comprises a vertical gear 65. Rotation of the pinion 66 in FIG. 7B thereby facilitates rotation about a horizontal (pitch) frame of reference, such as the articulating link member 36.

Figure 7C:
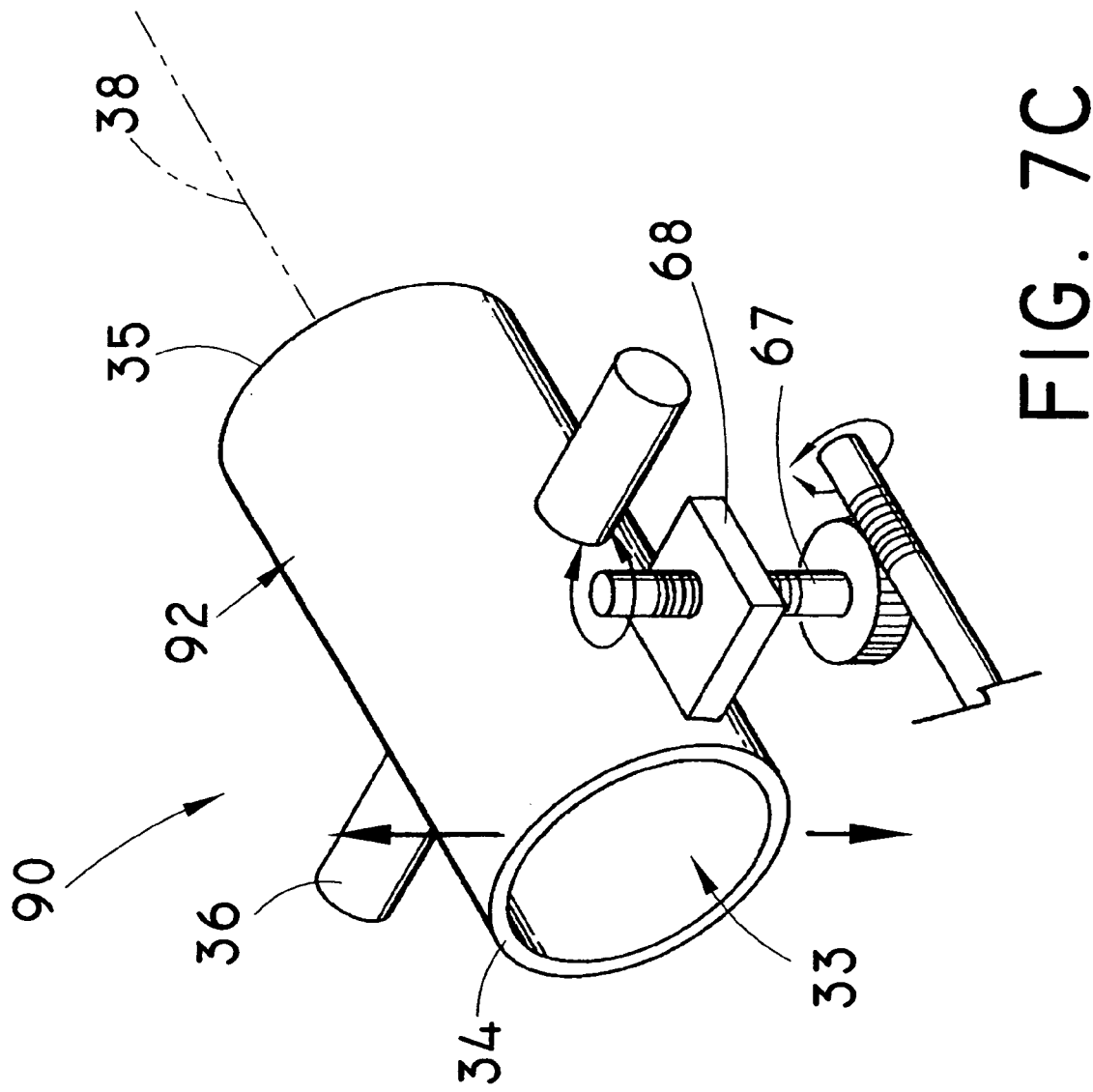
FIG. 7C is a perspective view of an alternative actuator embodiment having a jack screw actuator.

As another non-limiting example of an actuator 90, there may be used a jack screw arrangement as shown in FIG. 7C. With this embodiment of using a jack screw arrangement, a bolt is positioned between the first body (not shown) and second body 92 and behind a pivot pin (articulation link member). A bolt 67 is rotated in a threaded gear 68 upward and downward, which produces displacement of the proximal end of the second body 92 pivoting around a horizontal frame of reference, such as a pitch of the articulation link member 36.

FIG. 8A is a schematic side view of an alternative actuator 90 embodiment having a double acting pneumatic (or hydraulic) cylinder actuator 113. Actuation of the cylinder produces displacement of the second body 112. FIGS. 8B and 8C are schematic side views of an alternative actuator 90 embodiments, each comprising at least a single acting pneumatic (or hydraulic) cylinder actuator 114 with a return spring 115. FIG. 8B shows the spring 115 in a relaxed state, while FIG. 8C shows the return spring 115 in a pressured state supplying the force needed to return the second body to its original position.

As should be understood by one of ordinary skill in the art, actuators may utilize a variety of power sources including electronics, pneumatics, hydraulics, mechanics, or a combination of these power sources to cause the second body to move up-and-down, side-to-side, and/or more types degrees relative to a first body or a longitudinal axis of the first body. The power source may be located in the controller and/or the actuator. Furthermore, the actuator may utilize mechanically operated elements, electronically operated elements, electromechanically operated elements, pneumatically operated elements, hydraulically operated elements, piezoelectric stick-and-slip, thermomechanical, and chemomechanical elements.

For instance, an alternative embodiment of an actuator may be a motor and linkage system using a linear actuator rod. The motor connects to at least one linear actuator rotatably connected to at least one lever arm of the second body; as the linear actuator is extended or retracted this causes the lever arm to articulate the second body about a pivot point or axis and thereby adjust the incline or decline of the second body. Other actuators may utilize a rack and pinion system. Still others may use pneumatics (e.g., balloon) that cause the second body to tilt in a first direction as the pneumatic device is inflated, and to tilt in a second direction as the pneumatic device is deflated. Still, others may utilize hydraulic cables with pistons and cylinders. Other actuators may be cams wherein a rotating or sliding piece is in a mechanical linkage to transform rotary motion into linear motion or vice versa.

Methods

The invention also comprises methods of controlling position and/or orientation of the tool within the visual field beyond the distal opening of the endoscope by articulating the articulating main body attached to the distal end of the endoscope.

Figure 9:
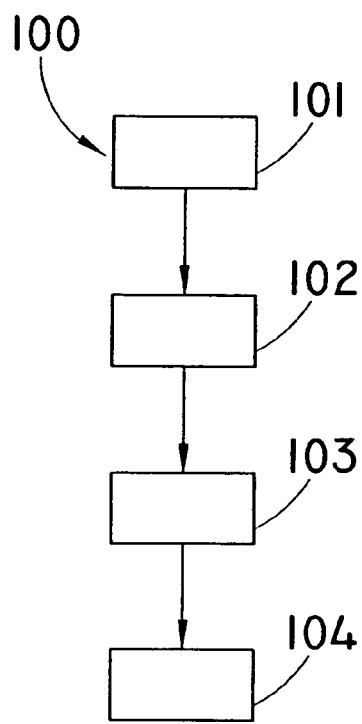
FIG. 9 is a block diagram illustrating a method of the invention.
Figure 10:
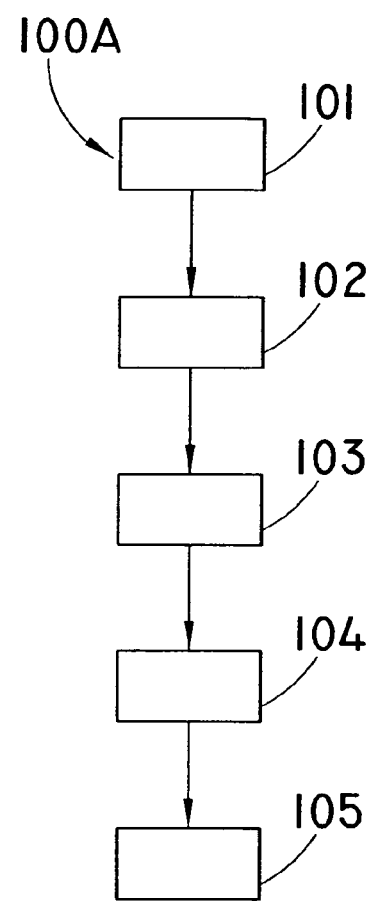
FIG. 10 is a block diagram illustrating another method of the invention.
Figure 11:
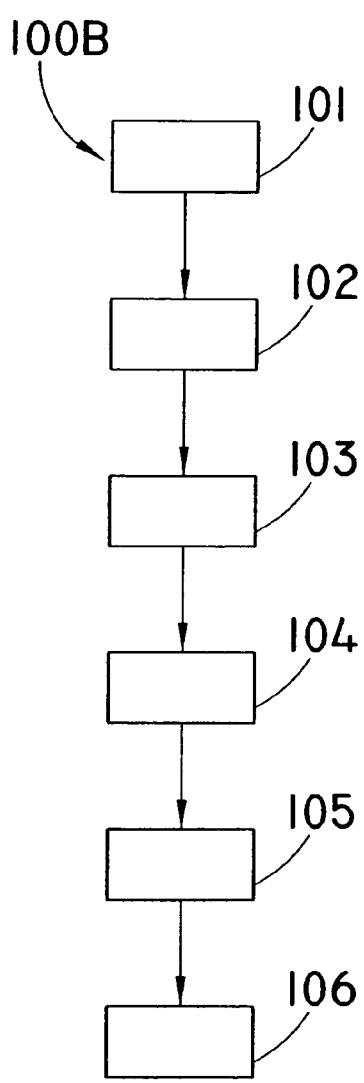
FIG. 11 is a block diagram illustrating an alternative embodiment of a method of the invention.

FIG. 9 shows method 100, an embodiment that comprises providing (step 101) an articulating main body having a stationary first body 31, 71, 81, an articulatable second body 32, 72, 82, 92, 112, and a coupler 19 articulatively joining—directly or indirectly in communication with—the second body to the first body as taught above. The first body has a distal end 31', 71', 81', a proximal end 31", 71", 81", and a first longitudinal axis 39. The second body has a proximal opening 34, 74 and a distal opening 35, 75 defining an accessory channel member passageway 33, 73, the distal opening having a second longitudinal axis 38, 89 oriented toward a space exterior to the first body distal end. In another step, the first body is detachably engaged (step 102) to a distal end portion 62 of an endoscope insertion section 61. The second body is articulated (step 103) in at least one degree of freedom relative to the first body. Optionally, an actuator 42, 90, 90' is provided (step 104) at or near the articulating main body and in communication with a controller 41. In another optional step (step 105) as shown in FIG. 10, an accessory channel member 11 having a first end 12 and a second end 13 is provided and received within the second body passageway 33, 73. In still another optional step as shown in FIG. 11, a support member 20 is provided (step 106), whereby the support member has a guide portion 21 and a base 23, the guide portion having proximal and distal openings 24, 25 and defining a passageway 22 configured to slidably receive the accessory channel member, the base having an insert abutting face 27 intermediate a pair of projections 28.

Another method comprises providing main body having first and second bodies, whereby the second body is a positioning member—as described above—with first and second ends and defining a lumen that secures an accessory channel member and having a distal opening (step 101). The articulating main body is attached to the distal end portion of the insert (step 102) and placed into the body, as through a mouth, orifice, or incision, and is positioned into place for an endoscopic procedure (step 103). The articulating main body is actuated so that the positioning member articulates (step 104).

In still another method 100A, as illustrated in FIG. 10, diagnostic, monitoring, scope, sewing device, cutting device, suturing device, forceps, grabbing device, or other instrument (collectively, "tool") may be inserted axially within the lumen of the accessory channel member (step 105). In yet another method 100B, as illustrated in FIG. 11, support members are provided such that the accessory channel member is slidably received in the a lumen of the support member and the support member is attached to an endoscope insertion section (step 106).

A method of controlling position and/or orientation of the tool does not need to be performed sequentially. For instance, steps may be eliminated or combined, such as when the endoscope insertion section (or sheath containing same) is made, used, or offered for sale with an articulating control member already attached (steps 101, 102). Furthermore, the articulating main body may be actuated (step 103) and then a tool axially inserted into the accessory channel (step 105). Also, the support members may be attached to the endoscope insertion section (step 106) before the articulating main body is detachably engaged to the distal end of the endoscope insertion section (102), before the accessory channel member is inserted into the patient, and before the articulating main body is actuated (103).

It is intended that the foregoing detailed description of the medical devices and methods of delivering tools into and controlling the orientation of the tools in a physician's endoscope observation field and working space be regarded as illustrative rather than limiting. It should be understood that it is the following claims, including all equivalents, that are intended to define the spirit and scope of this invention. Terms are to be given their reasonable meaning and like terms may be used interchangeably in the broadest sense to achieve a particular result. Therefore, the embodiment of any figure and features thereof may be combined with the embodiments depicted in other figures. Other features known in the art and not inconsistent with the structure and function of the present invention may be added to the embodiments.

While particular elements, embodiments and applications of the present invention have been shown and described, it will be understood, of course, that the invention is not limited thereto since modifications may be made by those skilled in the art, particularly in light of the foregoing teachings. Therefore, it is therefore contemplated by the appended claims to cover such modifications as incorporate those features which come within the spirit and scope of the invention.

What is claimed is:

1. An endoscopic surgical access device for detachably engaging an insertion section of an endoscope at or near a distal end portion of said insertion section, comprising:
    a stationary first body having a distal end, a proximal end, and a holding member, the holding member including at least one insert clipping projection defining an insert receiving cavity and having a first longitudinal axis and an insert abutting face;
    an articulatable second body having a proximal opening and a distal opening, the openings defining an accessory channel member passageway having a second longitudinal axis, the distal opening of a distal end of the second body oriented toward a space exterior to the first body distal end; and
    a coupler joining the second body to the first body, the coupler having a mounting member comprising an axis and an articulation link member comprising an axis, the mounting member and articulation link member configured to articulatively couple the second body to the first body about a common single point of articulation defined by the mounting member axis intersecting with the articulation link member axis,
    wherein the second body longitudinal axis is capable of articulating relative to the first body longitudinal axis and the common single point of articulation such that the second body has at least two degrees of rotational freedom about the common single point of articulation,
    wherein the articulating second body is capable of moving in at least two of x, y, and z coordinates about the single point of articulation relative to the first body longitudinal axis.

2. The device of claim 1 wherein the holding member comprises a clip.

3. The device of claim 1 wherein the holding member has a curved section.

4. The device of claim 1 wherein the holding member is generally U-shaped.

5. The device of claim 1 wherein the holding member is generally saddle-shaped.

6. The device of claim 1 wherein the second body is generally tubular.

7. The device of claim 1 wherein the second body is sized to slidably receive an accessory.

8. The device of claim 1 wherein the second body is sized to securably receive an accessory.

9. The device of claim 1 wherein the coupler comprises a ball and socket.

10. An endoscopic surgical access device, comprising:
    an accessory channel member having a proximal first end, a flexible distal second end, an intermediate section intermediate the first and second ends, and a tool receiving lumen;
    a support body having a guide portion and a base, the guide portion having proximal and distal openings and defining a passageway configured to slidably receive the accessory channel member, the base having an insert abutting face intermediate a pair of projections;
    an articulating main body having a first body, a second body having an accessory channel member passageway that contains the accessory channel member distal second end, and a coupler having a mounting member comprising an axis and an articulation link member comprising an axis, the mounting member and articulation link member configured to articulatively join the second body to the first body about a common single point of articulation defined by an intersection of the mounting member axis and the articulation link member axis such that the second body has at least two degrees of and rotational freedom about the common single point of articulation relative to a first body longitudinal axis; and an actuator located at or near the articulating main body, wherein the actuator is configured to articulate the second body relative to the first body such that the second body articulates relative to the first body.

11. The device of claim 10 wherein the accessory channel member is flexible.

12. The device of claim 10 wherein the support body projections further comprise a clip.

13. The device of claim 10 wherein the support body further comprises an auxiliary lumen.

14. The device of claim 10 wherein the first body comprises a distal end, a proximal end, and a first longitudinal axis, and wherein the second body comprises a proximal opening and a distal opening defining the accessory channel member passageway configured to receive the accessory channel member second end, the distal opening of a distal end of the second body having a second longitudinal axis oriented toward a space exterior to the first body distal end.

15. The device of claim 10 wherein the actuator is coupled to a connector in communication with a controller.

16. The device of claim 15 wherein the actuator further comprises an actuation mechanism selected from the group consisting of mechanically operated elements, electronically operated elements, electromechanically operated elements, pneumatically operated elements, hydraulically operated elements, piezoelectrically operated elements, thermomechanically, chemomechanically, operated elements, and photoelectrically operated elements.

17. A method of orienting an endoscopic surgical access device, comprising:

providing an endoscopic surgical access device comprising an articulating main body having a stationary first body, an articulatable second body, and a coupler comprising a mounting member and an articulation link member, the mounting member comprising an axis and the articulation link member comprising an axis that intersect at a point of articulation, the coupler articulatively joining the second body to the first body such that the second body has at least two degrees of rotational freedom about the point of articulation and such that the second body is capable of articulating in at least two of x, y, and z coordinates the first body having a distal end, a proximal end, and a first longitudinal axis, the second body having a proximal opening and a distal opening defining an accessory channel member passageway, the distal opening of a distal end of the second body having a second longitudinal axis oriented toward a space exterior to the first body distal end;

detachably engaging the first body to a distal end portion of an endoscope insertion section; and articulating the second body in at least two of x, y, and z coordinates relative to the first body, whereby any flexible endoscopic tool insertable within the second body accessory channel member passageway is movable in at least two of x, y, and z coordinates relative to the first body in response to the articulating second body.

18. The method of claim 17 further comprising providing an actuator at or near the articulating main body and in communication with a controller.

19. The method of claim 17 further comprising providing an accessory channel member having a proximal first end and a flexible distal second end and a lumen, and the second end received within the second body passageway.

20. The method of claim 19 further comprising providing a support member having a guide portion and a base, the guide portion having proximal and distal openings and defining a passageway configured to slidably receive the accessory channel member, and the base having an insert abutting face intermediate a pair of projections with the base abutting the endoscope insertion section.

21. The device of claim 1 wherein the coupler comprises a pitch-yaw system having two degrees of rotational freedom.

22. The device of claim 1 wherein the coupler comprises a pitch-yaw-roll system having multiple degrees of rotational freedom.

23. The method of claim 17 further comprising the step of providing an endoscopic tool having a flexible distal portion.

24. The method of claim 23 further comprising the step of inserting the flexible distal portion of the endoscopic tool within the second body accessory channel member passageway.

25. The device of claim 24 further comprising the step of extending the distal portion of the endoscopic tool beyond the distal opening of the second body.

26. The device of claim 24 further comprising the step of articulating the second body to control exit trajectory of the distal portion of the endoscopic tool relative to an endoscope observation field.

27. The method of claim 19 further comprising the step of providing an endoscopic tool having a flexible distal portion.

28. The device of claim 27 further comprising the step of inserting the flexible distal portion of the endoscopic tool within the accessory channel member lumen.

29. The device of claim 28 further comprising the step of extending the distal portion of the endoscopic tool beyond the distal opening of the second body.

30. The device of claim 28 further comprising the step of articulating the second body to control exit trajectory of the distal portion of the endoscopic tool relative to an endoscope observation field.

* * * * *